US009448195B2

(12) United States Patent
Moreno et al.

(10) Patent No.: US 9,448,195 B2
(45) Date of Patent: Sep. 20, 2016

(54) ELECTROPHYSIOLOGICAL RECORDING SYSTEM AND METHODS OF USING SAME

(75) Inventors: Alonso P. Moreno, Draper, UT (US); Gary S. Goldberg, Stratford, NJ (US); Abhijit Mondal, Salt Lake City, UT (US); Ian Harvey, Kaysvile, UT (US); Brian Baker, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 444 days.

(21) Appl. No.: 13/810,402

(22) PCT Filed: Jul. 15, 2011

(86) PCT No.: PCT/US2011/044128
§ 371 (c)(1),
(2), (4) Date: Mar. 28, 2013

(87) PCT Pub. No.: WO2012/009606
PCT Pub. Date: Jan. 19, 2012

(65) Prior Publication Data
US 2013/0196368 A1 Aug. 1, 2013

Related U.S. Application Data

(60) Provisional application No. 61/399,694, filed on Jul. 16, 2010.

(51) Int. Cl.
C12M 3/00 (2006.01)
C12M 1/00 (2006.01)
(Continued)

(52) U.S. Cl.
CPC .............. G01N 27/00 (2013.01); C12M 25/02 (2013.01); C12M 41/46 (2013.01)

(58) Field of Classification Search
CPC .... C12M 25/02; C12M 41/46; C12M 25/10; G01N 27/00

USPC ....................................... 435/287.1
See application file for complete search history.

(56) References Cited

U.S. PATENT DOCUMENTS 3,948,732 A * 4/1976 Haddad ................. C12M 23/24
435/293.2
5,563,069 A * 10/1996 Yang ...................... C12M 25/02
435/295.3

(Continued)

FOREIGN PATENT DOCUMENTS

WO WO 2009/114689 * 9/2009 ............... A61B 5/05
WO WO 2010/009307 * 1/2010

OTHER PUBLICATIONS

U.S. Appl. No. 61/399,694, filed Jul. 16, 2010, Alonso P. Moreno.
(Continued)

Primary Examiner — Nathan Bowers
(74) Attorney, Agent, or Firm — Ballard Spahr LLP

(57) ABSTRACT

Electrophysiological recording systems for analysis of cultured cells include an recording device and a housing for supporting the electrophysiological recording device. The device has a porous membrane with top and bottom surfaces and a plurality of pores extending between the top and bottom surfaces. The porous membrane defines a first cell culture region disposed on the top surface and an opposed second cell culture region disposed on the bottom surface. The electrophysiological recording device has a plurality of electrodes positioned on the porous membrane in between a first insulation layer and a second insulation layer. The plurality of electrodes extend to the first cell culture region of the porous membrane. Recording ends of the electrodes measure electrical properties of cells cultured within the first and second cell culture regions, while the contact ends of the electrodes are positioned in electrical communication with data acquisition equipment.

29 Claims, 21 Drawing Sheets

(51) Int. Cl.
G01N 27/00 (2006.01)
C12M 1/12 (2006.01)
C12M 1/34 (2006.01)

(56) References Cited

U.S. PATENT DOCUMENTS

| | | | | |
|---|---|---|---|---|
| 6,372,495 | B1* | 4/2002 | Flendrig | A61M 1/3472 435/177 |
| 6,398,932 | B1* | 6/2002 | Anderson et al. | 435/287.1 |
| 6,521,465 | B2* | 2/2003 | Stimpson | 435/287.1 |
| 2002/0063067 | A1* | 5/2002 | Bech et al. | 205/775 |
| 2004/0014077 | A1* | 1/2004 | Schultz et al. | 435/287.1 |
| 2010/0311599 | A1* | 12/2010 | Wheeler et al. | 435/287.1 |

OTHER PUBLICATIONS

PCT/US2011/044128 (WO 2012/009606), Jul. 15, 2011, Alonso P. Moreno.

Arndt, S. et al. "Bioelectrical impedance assay to monitor changes in cell shape during apoptosis." *Biosensors and Bioelectronics*;19:583-94. (2004).

Banach, K. et al. "Development of electrical activity in cardiac myocyte aggregates derived from mouse embryonic stem cells." *Am J Physiol Heart Circ Physiol*; 284:H2114-H2123. (2003).

Beeres, S.L., et al. "Human adult bone marrow mesenchymal stem cells repair experimental conduction block in rat cardiomyocyte cultures." *J Am Cull Cardio*;46(10):1943-52. (2005).

Camelliti, P., et al. "Fibroblast network in rabbit sinoatrial node. Structural and functional identification of homogeneous and heterogeneous cell coupling." *Circ Res*;28-835. (2004).

Chaytor, A.T. et al. "Connexin-mimetic peptides dissociate electrotonic EDHF-type signalling via myoendothelial and smooth muscle gap junctions in the rabbit iliac artery". *Br J Phatmacol*;144(1):108-14. (2005).

Christ, G.J., et al. "Gap junction-mediated intercellular diffusion of Ca2+ in cultured human corporal smooth muscle cells." *Am J Physiol*;263:C373-C383. (1992).

Cui, X., et al. "Human microvasculature fabrication using thermal inkjet printing technology." *Biomaterials*;30(31):6221-7). (2009).

Dai, W., et al. "The influence of structural design of PLGA/collagen hybrid scaffolds in cartilage tissue engineering." *Biomaterials*;2141-52. (2010).

Dora, K.A., et al. "Modulation of endothelial cell KCa3.1 channels during endothelium-derived hyperpolarizing factor signaling in mesenteric resistance arteries." *Circ Res* 23;102(10):1247-55. (2008).

Fast, V.G., et al "Microscopic conduction in cultured strands of neonatal heart cells measured with voltage-sensitive dyes." *Cir Res*;73(5):914-25. (1993).

Frey, U., et al. "Cell Recordings with a CMOS high-density microelectrode array." p. 167-170. (2007).

Gavrieli, Y., et al. "Identification of programmed cell death in situ via specific labeling of nuclear DNA fragmentation." *The Journal of Cell Biology*;119(3):493-501. (1992).

Goldberg, G.S., et al. "Capture of transjunctional metabolites." *Methods Mol Biol*;154:329-40. (2001).

Goldberg, G.S., et al. "Gap junctions between cells expressing connexin 43 or 32 show inverse permselectivity to adenosine and ATP." *J Boil CChem*;23:277(39):36725-30. (2002).

Griffith, A.J., et al. Cochleosaccular dysplasia associated with a connexin 26 mutation in keratitis-ichthyosis-deafness syndrome.: *Laryngoscope*;116(8):1404-8. (2006).

Griffith, T.M. "Endothelium-dependent smooth muscle hyperpolarization: do gap junctions provide a unifying hypothesis?" *Br J Pharmacol*;141(6):881-903. (2004).

Havla, J.B., et al. "Cartilage tissue engineering for auricular reconstruction: In vitro evaluation of potential genotoxic and cytotoxic effects of scaffold materials." *Toxicology in Vitro*;24(3):849-53. (2010).

Heberlein, K.R. et al. "Plasminogen activator inhibitor-1 regulates myoendothelial junction formation." *Circ Res*;106(6):1092-102. (2010).

Hecker, L., et al. "Engineering the heart piece by piece; state of the art in cardiac tissue engineering." *Regenerative Medicine*;2 (2): 125-44. (2007).

Heidi, Au H.T., et al. "Cell culture chips for simultaneous application of topographical and electrical cues enhance phenotype of cardiomyocytes." *Lab Chip*;9(4):564-75. (2009).

Hescheler, J., et al. "Embryonic stem cells as a model for the physiological analysis of the cardiovascular system." *Methods Molecular Biology*;185:169-87. (2002).

Hesketh, G.G., et al. "Ultrastructure and regulation of lateralized connexin43 in the failing heart." *Circ Res*;106(6):1153-63. (2010).

Isakson, B.E., et al. "Heterocellular contact at the myoendothelial junction influences gap junction organization." *Circ Res*;97(1):44-51. (2005).

Johnson, T.A., et al. "Fabrication, evaluation, and use of extracellular K+ and H+ ion-selective electrodes." *Am J Physiol Heart Circ Physiol*;258(4)H1224-H1231. (1990).

Kleber, A.G. et al. "Basic Mechanisms of cardiac impulse propagation and associated arrhythmias." *Physiol Rev*; 84(2):431-88. (2004).

Kohl, P., et al. "Electrical coupling of fibroblasts and myocytes: relevance for cardiac propagation." *J Electrocardiol*;38(4 Suppl):45-50. (2005).

Lasher, R., et al. "Towards modeling of cardiac micro-structure with catheter-based confocal microscopy: A novel approach for dye delivery and tissue characterization." *Medical Imaging, IEEE Transactions*;28(8):1156-64. (2009).

Li, J. et al. "Interstitial K+ concentration in active muscle after myocardial infarction." *Am J Physiol Heart Circ Physiol*;292(2):H808-H813. (2007).

Matchkov, V.V., et al. "Analysis of effects of connexin-mimetic peptides in rat mesenteric small arteries." *Am J Physiol Heart Circ Physiol*;292(1):H357-H367. (2006).

Ott H.C. et al. "Perfusion-decellularized matrix: using nature's platform to engineer a bioartificial heart". *Nat Med*;14(2):213-21. (2008).

Owens, G.K., et al. "Expression of smooth muscle-specific alpha-isoactin in cultured vascular smooth muscle cells: relationship between growth and cytodifferentiation." *The Journal of Cell Biology*;102;(2):343-52. (1986).

Pepper, M.E., et al. "Design and implementation of a two dimensional inkjet bioprinter." *Conf Proc IEEE Eng Med Biol Soc*;6001-5. (2009).

Rezwan, K., et al. "Biodegradable and bioactive porous polymer/inorganic composite scaffolds for bone tissue engineering" *Biomaterials*;(18):3413-31. (2006).

Sachse F.B., et al. "A model of electrical conduction in cardiac tissue including fibroblast." *Ann Biomed Eng*;36(1):41-56. (2009).

Salameh A, et al. "Cyclic mechanical stretch induces cardiomyocyte orientation and plarization of gap junction protein Connexin43." *Circ Res* 8;106(10):1592-602. (2010).

Sharma, V., et al. "Spatial heterogeneity of transmembrane potential responses of single guine-pig caria cells during electric field simulation." *Journal of Physiology*;542.2, p. 477-49. (2002).

Shi W, et al. "Endothelial responses to oxidized lipoproteins determine genetic susceptibility to atherosclerosis in mice." *Circulation* 4;102(1):75-81 (2000).

Sohn, K., et al. "The maximum downstroke of surface potential as an index of electrical coupling and propagation." *Exp Cell Res.* (2010).

Taccardi, B., et al. "Intramural activation and repolarization sequences in canine ventricles." Experimental and simulation studies. *Journal of Electrocardiology*;38(4, Supplement 1):131-7. (2005).

Thomas, J., et al. "Effects of induced post-ischemic phosphorylation on action potential propagation in mouse cardiomyocytes." *Biophysical Journal*;96[3], 283a Ref Type: Abstract. (2009).

(56) References Cited

OTHER PUBLICATIONS

Tiruppathi, C., et al. "Electrical method for detection of endothelial cell shape change in real time: assessment of endothelial barrier function." *Proc Natl Acad Sci*;89(17):7919-23. (1992).

Webb RC. Smooth muscle contraction and relaxation. *Advan Physiol Edu*;27(4):201-6. (2003).

Zhong, G., et al. "II-regulation of Cx43 cDNA expression enables gap junction single channel analysis." *Biotechniques*;34:1034-46. (2003).

Zlochiver, S., et al. "Electrotonic myofibroblast-to-myocyte coupling increases propensity to reentrant arrhythmias in two-dimensional cardiac monolayers." 95[9],4469-4480. 11-1-Ref type: Abstract. (2008).

* cited by examiner

EXPLODED VIEW

RECORDING MEMBRANE

TOP VIEW

ELECTROPHYSIOLOGICAL RECORDING SYSTEM AND METHODS OF USING SAME

CROSS-REFERENCE TO RELATED APPLICATIONS

This application is a National Phase Application of International Application No. PCT/US2011/044128, filed Jul. 15, 2011, which claims priority to U.S. Patent Application No. 61/399,694, filed Jul. 16, 2010, which applications are incorporated herein fully by this reference.

FIELD

The disclosed invention is generally related to analysis of cultured cells. More particularly, the disclosed invention is related to electrophysiological analysis of cellular interactions between two groups of cells, as well as the effects these cellular interactions have on the electrophysiological characteristics of each respective group of cells.

BACKGROUND

Measurement of extracellular signals from cells and tissues provides vital information in determining cellular excitability and conductive mechanisms. These signals are produced mostly by flow of ions like calcium ($Ca^+$), sodium ($Na^+$), potassium ($K^+$), and chloride ($Cl^-$) through cell membrane channels.

In vitro tissue biosynthesis is an invaluable resource not only for tissue-organ replacement, but also for studies of disease mechanisms as well as for building high-throughput cell bioassay systems or biochips for pharmacological and proteomic studies. In vitro biosynthesis of three-dimensional (3D) multi-cellular structures that resemble adult or differentiated tissue has been tried for many years with limited success, mostly because organs enclose more than one cell type and because the existing amorphous bio-compatible materials do not permit pre-arrangement of different cell types with their appropriate functional architecture.

Multi-Electrode Array (MEA) devices have facilitated recordings of extracellular electrical activity simultaneously from multiple sites, in vitro and in vivo. Current MEA devices are designed for culturing and recording from cells of one type or a mixture of different cell types combined in a two dimensional scheme. While a major fraction of bodily tissues are composed of two or more cell types (e.g. glia and neurons in the brain, fibroblasts, smooth muscle cells, endothelial cells and myocytes in the heart and endothelial and smooth muscle cells in the arteries), there are no viable systems for studying the three-dimensional interactions between such cells.

Electrical recordings in heart muscle can be made at surface cells using optical mapping or impaling glass microelectrodes. However, measurements at deeper layers require the use of plunge electrodes, which can induce tissue damage.

There are similar challenges associated with physiological studies of agonists, antagonists, and their corresponding receptors, such as in high-throughput drug screenings. Conventionally, such studies require the use of freshly isolated tissue samples, and results of the studies can be adversely impacted by ischemia and other factors.

Thus, there is a need for systems of studying preparations where two or more cell types can be co-cultured in a three-dimensional, controlled manner. There is a further need for using such systems in improving the understanding of cell interaction mechanisms and to improve the artificial development of tissues. There is still a further need for an in vitro reconstituted system in which the architecture for multiple cell layers and types is produced with an electrical recording system already in place. There is still a further need for a cell-based assay that permits performance of the high-throughput drug screenings and other physiological studies while avoiding the need for fresh tissue samples and limiting the likelihood of events that adversely affect such studies.

SUMMARY

Disclosed herein are electrophysiological recording systems for analysis of cultured cells. The disclosed electrophysiological recording systems include an electrophysiological recording device and a housing for supporting the electrophysiological recording device. In one aspect, the electrophysiological recording device has a porous membrane with top and bottom surfaces and a plurality of pores extending between the top and bottom surfaces. The porous membrane defines a first cell culture region disposed on the top surface and an opposed second cell culture region disposed on the bottom surface. In another aspect, the electrophysiological recording device has a plurality of electrodes positioned thereon the porous membrane in between a first insulation layer and a second insulation layer. The plurality of electrodes extend to the first cell culture region of the porous membrane. Recording ends of the electrodes measure electrical properties of cells cultured within the first and second cell culture regions, while the contact ends of the electrodes are positioned in electrical communication with data acquisition equipment.

In one aspect, the housing of the electrophysiological recording system defines a cell culture chamber. In this aspect, at least a portion of the porous membrane is mountable or otherwise configured for positioning within the cell culture chamber of the housing. In another aspect, the housing of the electrophysiological recording system includes a first base support portion for supporting a recording portion of the porous membrane, a second base support portion for supporting the contact portion of the porous membrane, and a first cover portion for attachment over the first base portion. The first base portion and the first cover portion define respective openings that cooperate to define the cell culture chamber. The second base support portion supports the contact portion of the porous membrane such that at least a portion of the cell culture region of the porous membrane, including the recording portion of the porous membrane, overlies the opening of the first base support portion. Optionally, the electrophysiological recording system includes means for rolling up the porous membrane to form a three-dimensional cell culture.

Also disclosed are methods for analyzing cells using the electrophysiological recording systems and devices described herein.

Also disclosed are methods of making tissue compositions using the electrophysiological recording systems and devices described herein.

Also disclosed are methods of forming the electrophysiological recording devices described herein.

BRIEF DESCRIPTION OF THE DRAWINGS

These and other features of the preferred embodiments of the invention will become more apparent in the detailed description in which reference is made to the appended drawings wherein:

FIG. 1 depicts an exploded view of an exemplary electrophysiological recording system as described herein.

FIG. 2 depicts another exemplary electrophysiological recording system as described herein.

FIG. 3 depicts another exemplary electrophysiological recording system as described herein.

FIG. 4 depicts an exemplary electrophysiological recording device as described herein.

FIG. 6 depicts the various stages in the fabrication of an exemplary electrophysiological recording device, as described herein.

FIG. 7 provides images of the recording ends of exemplary electrodes as described herein.

FIG. 8 depicts the use of an exemplary gear assembly having a central rod for rolling up the porous membrane to form a three-dimensional cell culture of two different groups of cells on opposite surfaces of a porous membrane that communicate across the porous membrane, as described herein. FIG. 8 further depicts the use of the rod to support the rolling up of the porous membrane and to permit recording of electrical properties of the two groups of cells following roll-up.

FIG. 10A depicts the experimental setup, while FIGS. 10B-10D are images demonstrating communication between cells located on opposite sides of the porous membrane.

FIG. 11 displays various recordings of cultured cardiomyocytes using an exemplary electrophysiological recording device as described herein.

DETAILED DESCRIPTION OF THE INVENTION

Figure 1A:
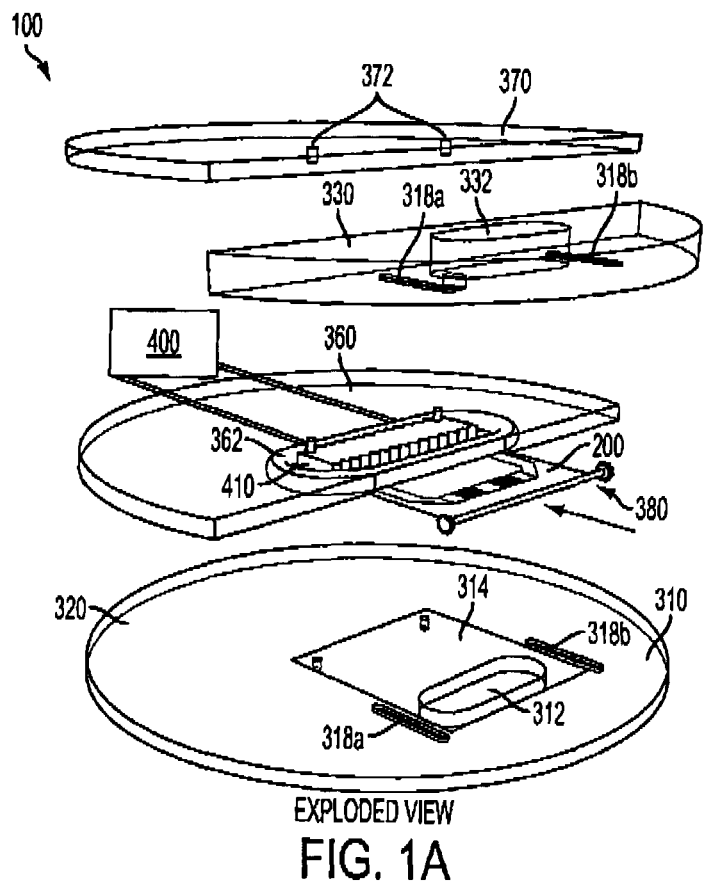
FIG. 1A is an exploded view of the exemplary electrophysiological recording system.
Figure 1B:
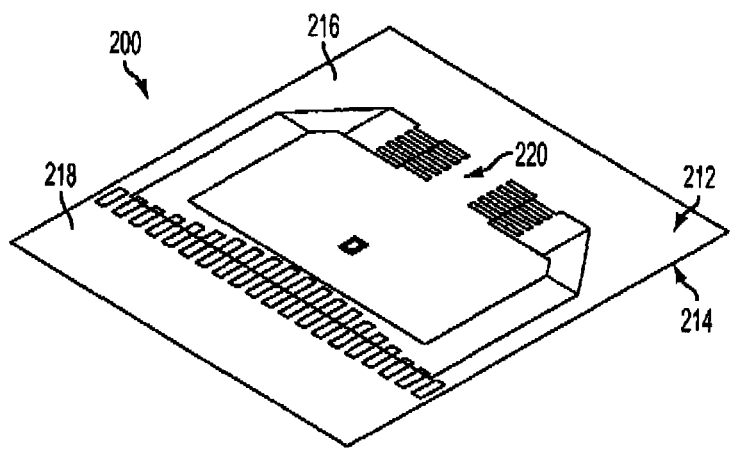
FIG. 1B is a perspective view of a recording device of the exemplary electrophysiological recording system of FIG. 1A.
Figure 1C:
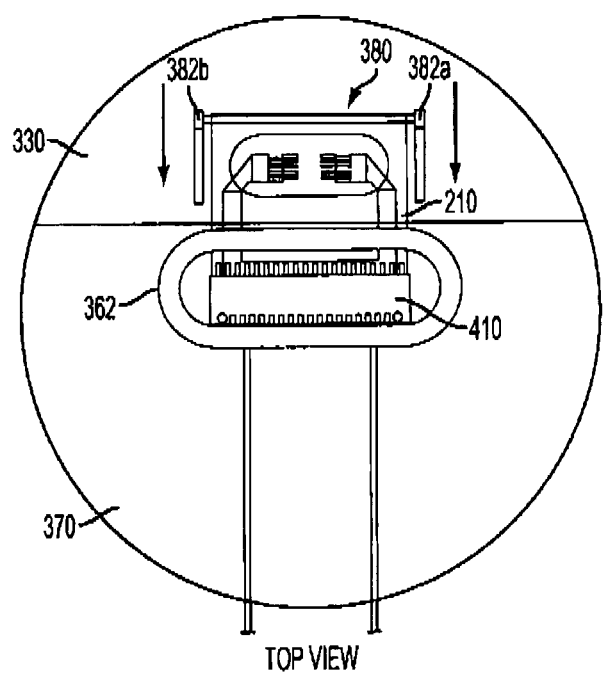
FIG. 1C is a partially transparent top view of the electrophysiological recording system of FIG. 1A.
Figure 1D:
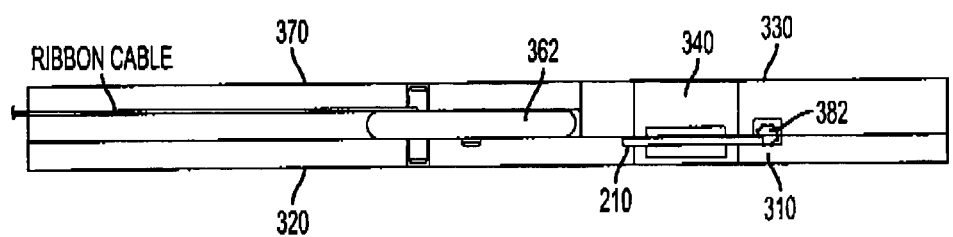
FIG. 1D is a partially transparent side view of the electrophysiological recording system of FIG. 1A.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an electrode" can include two or more such electrodes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "or" as used herein means any one member of a particular list and also includes any combination of members of that list.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

As used throughout, by "subject" is meant an individual. For example, a "subject" can be a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, rabbit, rat, guinea pig, etc.). For example, the subject is an animal. In certain embodiments, the subject is a human being. As used herein, a "subject" is the same as a "patient," and the terms can be used interchangeably.

Described herein is an electrophysiological recording system for analysis of cultured cells. With reference to FIGS. 1-6, the electrophysiological recording system 100 comprises an electrophysiological recording device 200 and a housing 300 for supporting the electrophysiological recording device. Methods of producing and using the electrophysiological recording system 100 are also described.

The Electrophysiological Recording Device

In one aspect, as shown in FIGS. 1-5, the electrophysiological recording device 200 can comprise a porous membrane 210 having a top surface 212 and an opposed bottom surface 214. In this aspect, the porous membrane 210 can define a first cell culture region disposed on a select portion of the top surface 212 and a second cell culture region disposed on a select portion of the bottom surface 214. It is contemplated that the first cell culture region can overlie and have a corresponding size and shape to the second cell culture region. Thus, the first and second cell culture regions are together labeled in the Figures as a single element 216, even though it is understood that the respective cell culture regions are located on opposite surfaces of the porous membrane 210. In another aspect, the porous membrane 210 can further define a plurality of pores 230 extending between the opposed first and second cell culture regions on the respective opposed top and bottom surfaces 212, 214.

It is contemplated that the top surface 212 of the porous membrane 210 can be configured to receive a first group of cells and that the bottom surface 214 of the porous membrane 210 can be configured to receive a second group of cells. Thus, in exemplary aspects, it is contemplated that the electrophysiological recording system 100 can comprise means for culturing cells on the top surface 212 and the bottom surface 214 of the porous membrane 210 within the first and second cell culture regions 216. In these aspects, it is contemplated that the means for culturing cells on the top surface 212 and the bottom surface 214 of the porous membrane 210 can comprise any known means for applying and culturing cells on a selected surface. It is further contemplated that the top and bottom surfaces 212, 214 of the porous membrane 210 can be selectively coated with one or more physiological substrates, such as, for example and without limitation, collagen, laminin, and the like, to increase cellular adhesion without compromising intercellular communication.

In a further aspect, the porous membrane 210 can comprise polycarbonate. In an exemplary aspect, the porous membrane 210 can be a polycarbonate track etch (PCTE) manufactured by STERLITECH CORPORATION. In another exemplary aspect, the porous membrane 210 can comprise a biodegradable material. In a further exemplary aspect the porous membrane 210 can comprise a bioabsorbable material.

In an additional aspect, the porous membrane 210 can have a thickness ranging from about 1 micrometer to about 20 micrometers, more preferably from about 5 micrometers to about 15 micrometers, and, most preferably from about 8 micrometers to about 12 micrometers. In an exemplary aspect, it is contemplated that the thickness of the porous membrane 210 can be about 10 micrometers. In another aspect, each pore 230 of the plurality of pores of the porous membrane 210 can have a diameter ranging from about 0.5 micrometers to about 15 micrometers, more preferably from about 1 micrometer to about 10 micrometers, and most preferably from about 2 micrometers to about 5 micrometers. In an exemplary aspect, it is contemplated that each pore 230 of the plurality of pores of the porous membrane 210 can have a diameter of about 3 micrometers. In a further aspect, the plurality of pores 230 of the porous membrane 210 can be randomly scattered or otherwise present within the opposed cell culture regions 216 at a density ranging from about 100,000 pores per square centimeter to about 300,000 pores per square centimeter, more preferably from about 150,000 pores per square centimeter to about 250,000 pores per square centimeter, and most preferably from about 175,000 pores per square centimeter to about 225,000 pores per square centimeter. In an exemplary aspect, the plurality of pores 230 of the porous membrane 210 can be randomly scattered or otherwise present within the opposed cell culture regions 216 at a density of about 200,000 pores per square centimeter.

It is contemplated that the plurality of pores 230 can be sized and positioned such that cultured cells on the top surface 212 of the porous membrane 210 can communicate with cultured cells on the opposed bottom surface 214 of the porous membrane without the cultured cells on the top or bottom surface migrating across the porous membrane through the plurality of pores. It is further contemplated that the plurality of pores 230 can permit formation of gap junctions between the cultured cells on the opposed top and bottom surfaces 212, 214 of the porous membrane 210. It is further contemplated that the plurality of pores 230 of the porous membrane 210 can be configured to permit communication between cultured cells on the top surface 212 and bottom surface 214 of the porous membrane for three or more weeks. It is still further contemplated that, upon submersion of the porous membrane 210 in a cell culture medium within a conventional culture and/or recording chamber, the plurality of pores 230 can prevent the occurrence of ischemia in cultured cells on the top or bottom surface 212, 214 of the porous membrane. It is still further contemplated that the ability of the disclosed electrophysiological recording system 100 to maintain intercellular communication between the layers of the porous membrane 210, whether direct (gap junctions) or indirect (paracrine), can improve and promote maintenance of tissue homeostasis during cell culturing.

Figure 5:
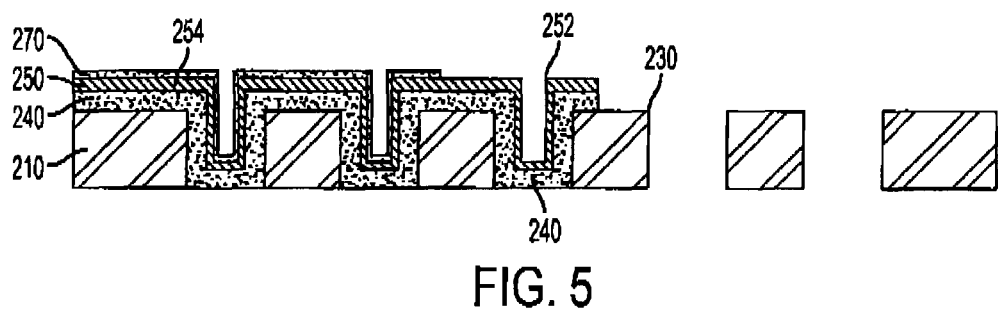
FIG. 5 depicts a cross-sectional side view of the various layers of an exemplary electrophysiological recording device, as described herein.

In an additional aspect, the electrophysiological recording device 200 can comprise a first insulation layer 240. In this aspect, the first insulation layer 240 can be positioned thereon at least a portion of the porous membrane 210. In one aspect, the first insulation layer 240 can be applied thereon the top surface 212 of the porous membrane 210 and therein at least a portion of the pores 230 defined by the porous membrane. In this aspect, as shown in FIG. 5, it is contemplated that the first insulation layer 240 can be applied as a continuous layer across at least a portion of the top surface 212 of the porous membrane 210 and within and across at least a portion of the pores 230 defined by the porous membrane. Thus, it is contemplated that the first insulation layer can extend from the top surface of the porous membrane into a pore along walls of the pore and across a bottom portion of the pore substantially at the interface between the pore and the second surface of the porous membrane. In an exemplary aspect, the first insulation layer 240 can be applied across substantially the entire top surface of the porous membrane. In this aspect, it is contemplated that the first insulation layer 240 can be applied thereon or within at least a portion of each pore of the plurality of pores 230 defined by the porous membrane 210.

In a further aspect, the first insulation layer 240 can have a thickness ranging from about 100 nm to about 1 µm, more preferably from about 200 nm to about 800 nm, and most preferably from about 300 nm to about 700 nm. In an exemplary aspect, the first insulation layer 240 can have a thickness of about 500 nm. Optionally, in an exemplary aspect, the first insulation layer 240 can comprise parylene, including, for example and without limitation, Parylene C, Parylene AF-4, Parylene SF, and Parylene HT.

In another aspect, and with reference to FIG. 4, the electrophysiological recording device 200 can comprise an electrode array comprising a plurality of electrodes 250. In this aspect, each electrode 250 of the plurality of electrodes can have a distal recording end 252, a lead portion 254, and a proximal contact end 256. In an additional aspect, the plurality of electrodes 250 can be positioned thereon the porous membrane 210 and the first insulation layer 240 such that each electrode of the plurality of electrodes extends to the first cell culture region 216 of the porous membrane.

It is contemplated that the recording ends 252 of the plurality of electrodes 250 can be configured for measurement of electrical properties of cells cultured within the first and second cell culture regions 216 on the respective opposed top and bottom surfaces 212, 214 of the porous membrane 210. It is further contemplated that the recording ends 252 of the plurality of electrodes 250 can be configured to measure extracellular currents produced by action potentials of any excitable cell, such as, for example and without limitation, muscle cells and neurons. It is still further contemplated that, through appropriate distribution of the plurality of electrodes, the recording ends 252 of the plurality of electrodes 250 can be configured to measure tissue impedance, which can be indicative of the tightness and/or density of a particular tissue. It is still further contemplated that an ion-sensitive electrode having ionic-exchange-sensitive resins can be incorporated into the electrophysiological recording system 100 to permit measurement of voltage changes, which can be indicative of extracellular pH or other ionic concentrations.

It is further contemplated that the contact ends 256 of the plurality of electrodes 250 can be configured for electrical communication with data acquisition equipment 400 using any known electrical communication means. In an exemplary aspect, the contact ends 256 of the plurality of electrodes 250 can be configured for attachment to a one-piece electrical connector 410, such as, for example and without limitation, a SAMTEC SEI one-piece interface manufactured by SAMTEC, Inc. In this aspect, it is contemplated that the one-piece electrical connector 410 can be connected to additional data acquisition equipment 400 using known electrical communication means, including, for example and without limitation, ribbon cables and the like. It is further contemplated that the one-piece electrical connector 410 can have a plurality of pins, such as, for example and without limitation, 25 pins, that are configured for electrical connection to respective contact ends 256 of the plurality of electrodes 250. In exemplary aspects, the contact ends 256 of the plurality of electrodes 250 can be secured thereto a contact portion 218 of the porous membrane.

Figure 4A:
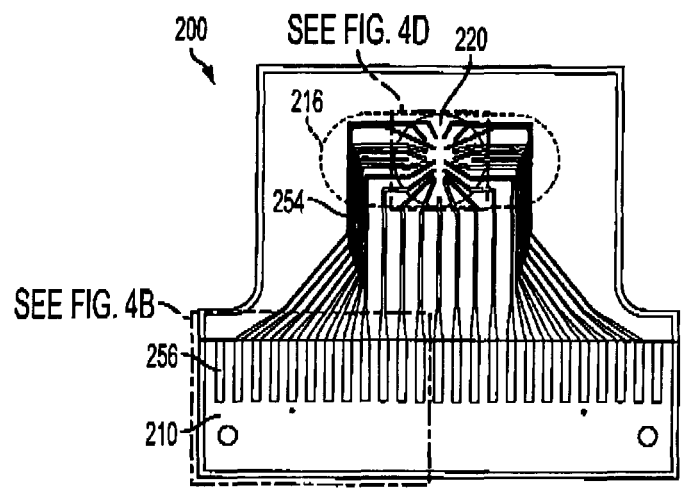
FIG. 4A is a top view of the exemplary electrophysiological recording device.
Figure 4B:
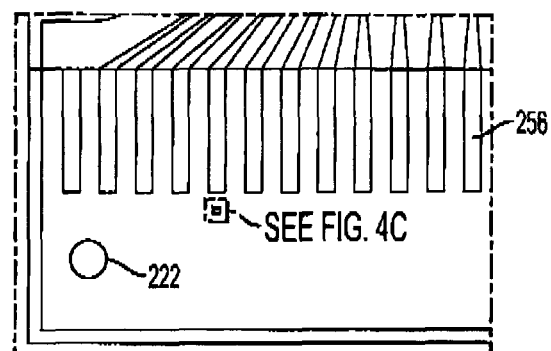
FIG. 4B is a close-up view of an alignment hole of the electrophysiological recording device of FIG. 4A.
Figure 4C:
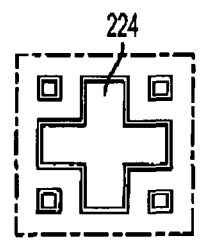
FIG. 4C is a close-up view of an alignment marker of the electrophysiological recording device of FIG. 4A.
Figure 4D:
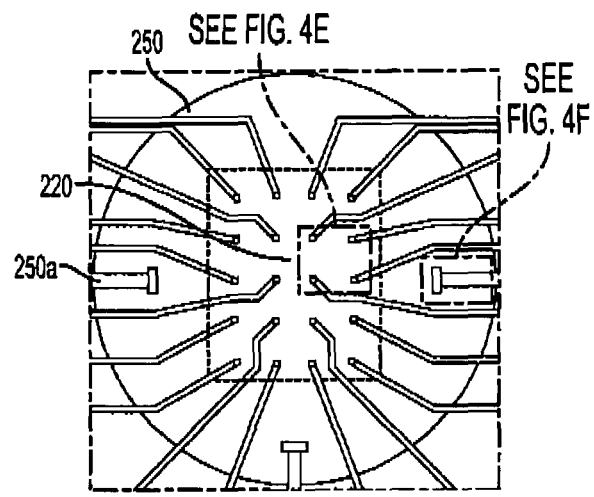
FIG. 4D is a close-up view of a cell culture region of the porous membrane of the electrophysiological recording device of FIG. 4A.
Figure 4E:
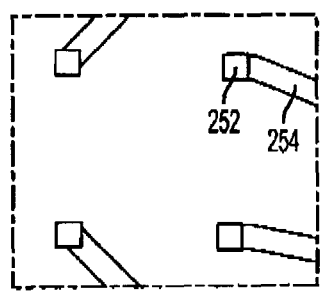
FIG. 4E is a close-up view of the recording ends of the electrodes of the electrophysiological recording device of FIG. 4A.
Figure 4F:
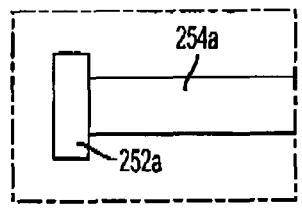
FIG. 4F is a close-up view of a stimulating electrode of the electrophysiological recording device of FIG. 4A.

In another aspect, it is contemplated that portions of the first and second cell culture regions 216 proximate the recording ends 252 of the plurality of electrodes 250 can define a recording portion 220 of the of the porous membrane 210. It is contemplated that the recording portion 220 can comprise a substantially circular region having a diameter ranging from about 1 mm to about 15 mm, more preferably from about 2 mm to about 10 mm, and most preferably from about 4 mm to about 6 mm. In an exemplary aspect, the recording portion 220 can comprise a substantially circular region having a diameter of about 5 mm. In an exemplary aspect, a central portion of the recording portion 220 of the porous membrane 210 can correspond to an area where no electrodes are positioned In a further aspect, as shown in FIG. 4B, the contact portion 218 of the porous membrane 210 can comprise one or more alignment holes 222. In this aspect, it is contemplated that the one or more alignment holes 222 of the contact portion 218 can be configured for alignment with one or more corresponding holes 412 defined therein the one-piece electrical connector 410, thereby permitting connection between the porous membrane 210 and the one-piece electrical connector 410 by insertion of a conventional pin or other fastener through each alignment hole of the contact portion and its corresponding hole in the electrical connector. In still a further aspect, as shown in FIG. 4C, the contact portion 218 of the porous membrane 210 can comprise one or more alignment markers 224. In this aspect, it is contemplated that the one or more alignment markers 224 can correspond to guide markings that confirm proper alignment of the porous membrane 210 during application of the electrodes and various layers of the electrophysiological recording device 200 as described herein.

In still a further aspect, the electrophysiological recording device 200 can comprise a supporting film proximate one or more edges of the porous membrane 210. It is contemplated that the supporting film can stabilize and protect the porous membrane 210 during handling while also providing further insulation to the contact ends 256 of the plurality of electrodes 250. In an exemplary aspect, the supporting film can be KAPTON™ tape or film manufactured by DUPONT.

In one aspect, the lead portion 254 of each electrode 250 of the plurality of electrodes can have a width ranging from about 10 μm to about 100 μm, more preferably from about 25 μm to about 75 μm, and most preferably from about 40 μm to about 60 μm. In an exemplary aspect, the lead portion 254 of each electrode 250 of the plurality of electrodes can have a width of about 50 μm. It is contemplated that, because the pores 230 of the porous membrane 210 can be randomly spaced within the recording portion 220, the pores in some areas of the recording portion can be closer to one another than in other areas of the recording portion. It is further contemplated that, in the areas of the recording portion 220 with a greater concentration of pores 230, the electrical resistance will be higher than in areas of lesser pore concentration. It is still further contemplated that the width of the recording ends 252 and the lead portions 254 of the plurality of electrodes 250 can be selected to avoid such high resistance areas of the recording portion 220 while still providing sufficient conduction of electrical signals generated within the recording portion.

In another aspect, the recording end 252 of each electrode 250 of the plurality of electrodes can have a width ranging from about 50 μm to about 200 μm, more preferably from about 75 μm to about 150 μm, and most preferably from about 90 μm to about 110 μm. In an exemplary aspect, the recording end 252 of each electrode 250 of the plurality of electrodes can have a width of about 100 μm. In one aspect, the respective contact ends 256 of adjacent electrodes of the plurality of electrodes can be spaced apart from one another at at least one predetermined distance, and the respective recording ends of adjacent electrodes of the plurality of electrodes are spaced apart from one another at at least one predetermined distance. In this aspect, within the recording portion 220, it is contemplated that the respective recording ends 252 of the plurality of electrodes 250 can be spaced apart from recording ends of adjacent electrodes by a distance ranging from between about 100 μm to about 1 mm, more preferably from about 250 μm to about 750 μm, and most preferably from about 400 μm to about 600 μm. In an exemplary aspect, within the recording portion 220, the respective recording ends 252 of the plurality of electrodes 250 can be spaced apart from the recording ends of adjacent electrodes by about 500 μm. It is further contemplated that the contact ends 256 of the plurality of electrodes 250 can be spaced apart from one another within the contact portion 218 of the porous membrane 210 by at least 500 μm. In a further aspect, the contact ends 256 of the plurality of electrodes 250 can have a width ranging from about 250 μm to about 750 μm, more preferably from about 350 μm to about 650 μm, and most preferably from about 400 μm to about 600 μm.

In an exemplary aspect, the contact ends 256 of the plurality of electrodes 250 can have a width of about 500 μm. In yet another aspect, it is contemplated that the lengths of the contact ends 256 of the plurality of electrodes 250 can be varied as necessary for connection thereto the data acquisition equipment 400. In this aspect, it is contemplated that the lengths of the contact ends 256 of the plurality of electrodes 250 can be greater than about 2 mm. It is further contemplated that the lengths of the contact ends 256 of the plurality of electrodes 250 can be greater than about 3 mm.

In a further aspect, it is contemplated that each electrode 250 of the plurality of electrodes can have any cross-sectional profile, including, for example and without limitation, a square, rectangular, circular, or elliptical profile. However, it is further contemplated that electrodes 250 having a square or rectangular profile can be more quickly and efficiently produced than electrodes having a circular or elliptical profile.

In an additional aspect, the electrophysiological recording system 100 can comprise means for inducing an action potential in cells cultured within at least one of the first cell culture region and the second cell culture region. In an exemplary aspect, and with reference to FIG. 4F, the means for inducing an action potential can comprise at least one stimulating electrode 250*a* among the plurality of electrodes 250 that is configured to stimulate electrical activity within the recording portion 220 of the porous membrane 210. In this aspect, the recording end 252*a* of the at least one stimulating electrode 250*a* can have a width of 100 μm to about 600 μm, more preferably from about 200 μm to about 400 μm, and most preferably from about 250 μm to about 350 μm, and the lead portion 254*a* of the at least one stimulating electrode can have a width ranging from about 50 μm to about 300 μm, more preferably from about 100 μm to about 200 μm, and most preferably from about 125 μm to about 175 μm. In an exemplary aspect, the recording end 252*a* of the at least one stimulating electrode 250*a* can have a width of about 300 μm, and the lead portion 254*a* of the at least one stimulating electrode can have a width of about 150 μm. In another exemplary aspect, it is contemplated that the plurality of electrodes 250 can comprise 23 electrodes, with three of the electrodes being stimulating electrodes. In a further aspect, it is contemplated that the plurality of electrodes 250, as well as the at least one stimulating electrode, can be arranged symmetrically within the recording portion 220 of the porous membrane 210.

In another exemplary aspect, the means for inducing an action potential can comprise one or more field electrodes. In this aspect, the one or more field electrodes can be plaques of wires of any suitable conductive material, such as, for example and without limitation, platinum, that are immersed in a cell culture solution close to the cultured cells. It is contemplated that the means for inducing an action potential can further comprise an external amplifier for providing a current of appropriate magnitude through the one or more field electrodes to trigger an action potential. The distance between the one or more field electrodes can be selectively varied depending on the particular cell type to be stimulated. In an exemplary aspect, it is contemplated that one or more field electrodes can be used to induce an action potential in cultured cells using the method described in V. Sharma and L Tung, "Spatial Heterogeneity of transmembrane potential responses of single guine-pig cardiac cells during electric field stimulation," Journal of Physiology (2002), 542.2, pp 477-492, the disclosure of which is hereby incorporated by reference herein in its entirety.

In a further exemplary aspect, the means for inducing an action potential can comprise a light source. In this aspect, the light source, such as, for example and without limitation, a ultraviolet (UV) light source, can trigger action potentials in the cultured cells. It is contemplated that the cultured cells can comprise cells that are transfected with ChannelRhodopsin (such as ChannelRhodopsin-1, ChannelRhodpsin-2, or Volvox ChannelRhodopsin) or another composition with light-gated ion channels. For example, in one application, Hela cells expressing Cx43 and transfected with ChannelRhodopsin-2 can be cultured on an opposite surface of the porous membrane from myocytes. HeLa cells can form junctions with the myocytes, and a flash of UV light can open the light-gated ion channels of the ChannelRhodopsin, which in turn trigger action potentials in the myocytes. An exemplary method of inducing an action potential in cells using ChannelRhodopsin-2 is described in Boyden, E S, Zhan, F., Bamberg, E. nagel, G. and Deisseroth, K. Nat. Neurosci. 8, 1263-1268 (2005), the disclosure of which is hereby incorporated by reference herein in its entirety.

In still another aspect, the plurality of electrodes 250 can comprise gold. In this aspect, it is contemplated that the plurality of electrodes 250 can comprise gold and one or more elements for promoting adhesion of the electrodes to the first insulation layer 240 and/or the porous membrane 210. In an exemplary aspect, the plurality of electrodes 250 can comprise gold, titanium oxide, and titanium, with the gold being applied over titanium oxide that has been applied over titanium. It is contemplated that the high conductivity, chemical inertness, and malleability of gold make it a desirable material for forming the plurality of electrodes 250. However, it is contemplated that any known material for forming electrodes can be used within the scope of the disclosed electrophysiological recording device.

In a further aspect, the electrophysiological recording device 200 can comprise a second insulation layer 270. In this aspect, the second insulation layer 270 can be positioned thereon each electrode 250 of the plurality of electrodes such that at least a portion of each electrode is positioned therebetween the first insulation layer 240 and the second insulation layer 270. It is contemplated that the second insulation layer 270 can be positioned thereon each electrode 250 of the plurality of electrodes such that only the lead portion 254 of each electrode is positioned therebetween the first insulation layer 240 and the second insulation layer. In other words, it is contemplated that the second insulation layer 270 can be applied such that the lead portion 254 of each electrode is insulated from the top and bottom and the recording end 252 and contact end 256 of each electrode are only insulated from the bottom.

In one aspect, the second insulation layer 270 can be applied thereon the plurality of electrodes 250 and a portion of the first insulation layer 240. As shown in FIGS. 6K-6L, it is contemplated that the second insulation layer can comprise a plurality of spaced insulation elements 272 that are configured to substantially completely overlie the plurality of electrodes 230. In another aspect, each insulation element 272 of the plurality of spaced insulation elements of the second insulation layer 270 can have a width ranging between about 25 µm to about 125 µm, more preferably from about 40 µm to about 100 µm, and most preferably from about 60 µm to about 80 µm. In an exemplary aspect, each insulation element 272 of the plurality of spaced insulation elements of the second insulation layer 270 can have a width of about 70 µm. It is contemplated that the widths of the plurality of insulation elements 272 of the second insulation layer 270 can be greater than the widths of the plurality of electrodes 250 to ensure complete insulation of the electrodes.

In a further aspect, the second insulation layer 270 can have a thickness ranging from about 100 nm to about 1 µm, more preferably from about 200 nm to about 800 nm, and most preferably from about 300 nm to about 700 nm. In an exemplary aspect, the second insulation layer 270 can have a thickness of about 500 nm. Optionally, in an exemplary aspect, the second insulation layer 270 can comprise parylene, including, for example and without limitation, Parylene C, Parylene AF-4, Parylene SF, and Parylene HT.

Methods of Producing the Disclosed Electrophysiological Recording Device

Figure 6A:
FIG. 6A is a side perspective view of a glass slide.
Figure 6B:
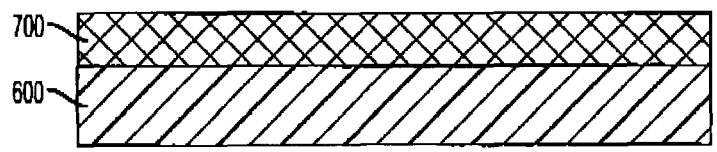
FIG. 6B is a side perspective view of a wafer formed by the application of a photoresist layer to the glass slide.
Figure 6C:
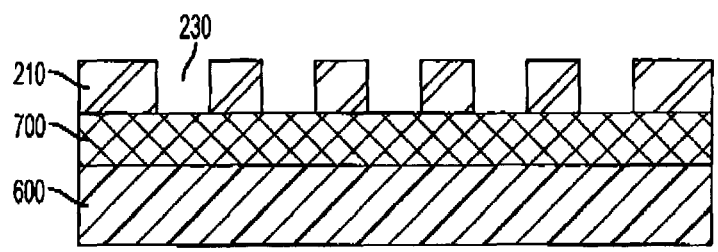
FIG. 6C is a side perspective view of the wafer after a porous membrane has been applied to the photoresist layer.
Figure 6D:
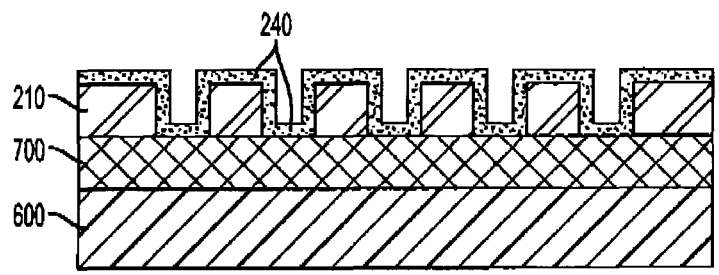
FIG. 6D is a side perspective view of the wafer after a first insulation layer has been applied to the porous membrane.
Figure 6E:
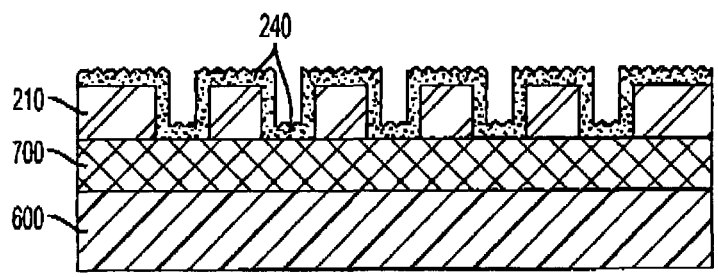
FIG. 6E is a side perspective view of the wafer after the first insulation layer has been roughened through an etching process.
Figure 6F:
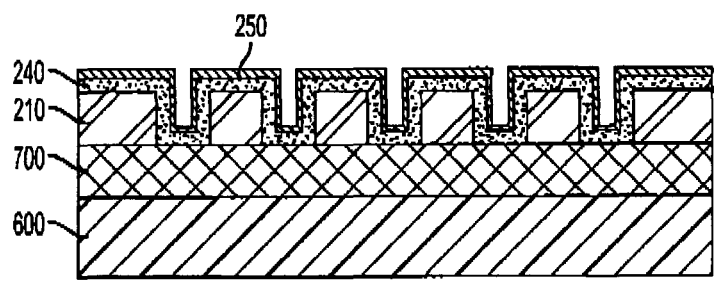
FIG. 6F is a side perspective view of the wafer after a layer of gold has been applied to the first insulation layer and the porous membrane.
Figure 6G:
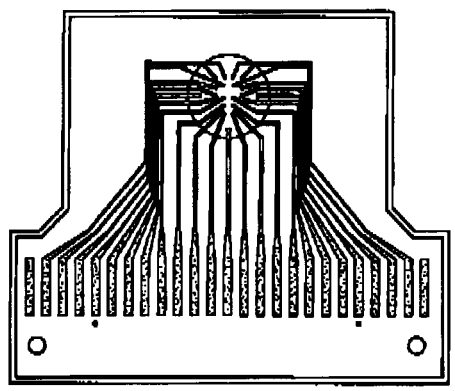
FIG. 6G is a side perspective view of an exemplary mask pattern for forming a plurality of electrodes from the layer of gold.
Figure 6H:
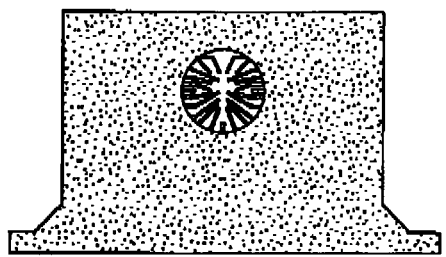
FIG. 6H is a side perspective view of an exemplary mask pattern for forming an insulation layer of the electrophysiological recording device.
Figure 6I:
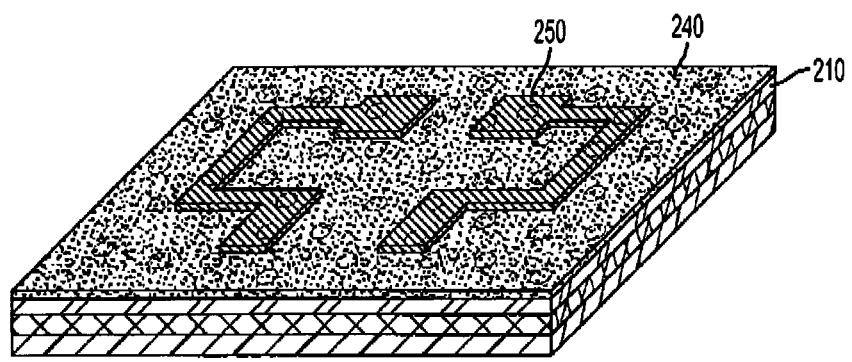
FIG. 6I is a side perspective view of the wafer after patterning of the plurality of electrodes.
Figure 6J:
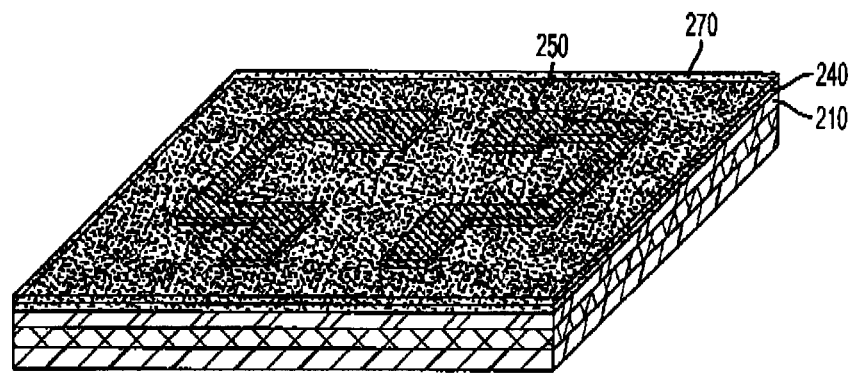
FIG. 6J is a side perspective view of the wafer after a second insulation layer is applied to the plurality of electrodes.
Figure 6K:
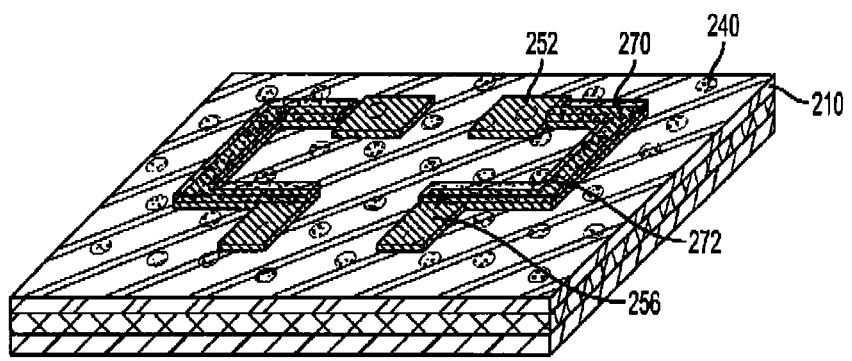
FIG. 6K is a side perspective view of the wafer following etching of the second insulation layer.
Figure 6L:
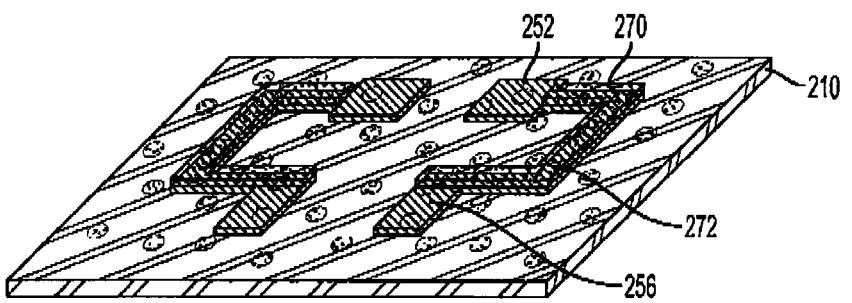
FIG. 6L is a side perspective view of the electrophysiological recording device after separation from the glass slide and photoresist layer.
Figure 7A:
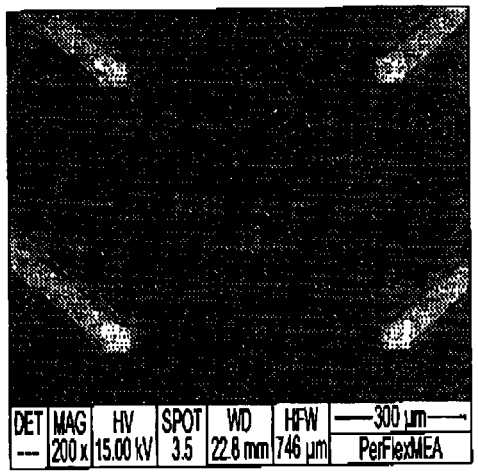
FIG. 7A is a microscopic image (200× magnification) of four exemplary electrodes within the recording portion of a porous membrane as described herein.
Figure 7B:
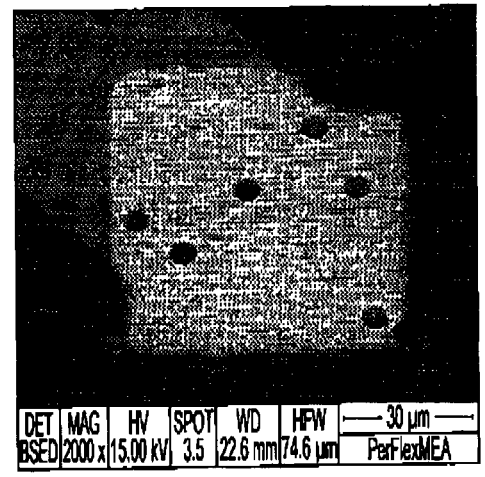
FIG. 7B is a microscopic image (2,000× magnification) of the recording end of one of the exemplary electrodes depicted in FIG. 7A.

With reference to FIGS. 6A-6L, methods of producing the electrophysiological recording device 200 are also disclosed. In one aspect, a method of producing the electrophysiological recording device can comprise securing the porous membrane to a rigid substrate 600. In this aspect, as depicted in FIG. 6A, it is contemplated that the rigid substrate 600 can be, for example and without limitation, a conventional glass or plastic slide. It is further contemplated that the porous membrane can be cut to an appropriate size for overlying the rigid substrate 600.

In an exemplary aspect, as shown in FIGS. 6B-6C, the step of securing the porous membrane to the rigid substrate can comprise applying a photoresist layer 700 to the rigid substrate and then securing the porous membrane to the photoresist layer 700 such that the porous membrane is coupled to the rigid substrate 600. In this aspect, it is contemplated that the photoresist layer can have an appropriate viscosity for attaching the porous membrane to the rigid substrate while also blocking the pores of the porous membrane from the bottom. In one aspect, the photoresist layer can comprise, for example and without limitation, AZ 4620 photoresist. In an exemplary aspect, the photoresist layer can be spun on the rigid substrate at about 2,500 rpm for about 50 seconds. In another exemplary aspect, it is contemplated that the photoresist layer can have a thickness ranging from about 8 to about 10 µm. After the photoresist layer is applied to the rigid substrate, it is contemplated that the resulting wafer can be baked at about 90° C. for about five minutes on a hot plate to provide the photoresist layer with a smooth and uniform surface. It is contemplated that binding of the porous membrane to a rigid substrate can form a wafer that is ideal for lithography and configured to block the pores of the porous membrane such that only one surface of the porous membrane can be coated.

In a further exemplary aspect, after the porous membrane is applied to the photoresist layer, the resulting wafer (with the porous membrane) can be baked, thereby stretching the porous membrane and generating bubble-like wrinkles on the porous membrane. In this aspect, the wrinkles on the porous membrane can be wiped off proximate the edges of the porous membrane. In an additional aspect, after the wrinkles on the porous membrane are removed, the wafer can be cooled.

In another aspect, and with reference to FIG. 6D, the method of producing the electrophysiological recording device can comprise coating the top surface of the porous membrane with the first insulation layer through a low pressure vapor deposition process (LPCVD). In this aspect, the porous membrane can be coated on all exposed surfaces, including the walls of the pores. It is contemplated that the coating of the top surface of the porous membrane using this isotopic process can block the pores of the porous membrane from the bottom surface of the porous membrane, thereby insulating any additional layers that are deposited on the first insulation layer from the bottom surface of the porous membrane.

In a further aspect, as shown in FIG. 6E, the method of producing the electrophysiological recording device can comprise dry etching the first insulation layer to roughen a top surface of the first insulation layer, thereby improving adhesion of layers applied on top of the first insulation layer. In an exemplary aspect, it is contemplated that the first insulation layer can be dry etched for about 30 s using oxygen as the etching gas.

In another aspect, the method of producing the electrophysiological recording device can comprise depositing one or more elements for promoting adhesion of the electrodes to the first insulation layer. In this aspect, it is contemplated that a multi-cathode sputtering system can be used to deposit the one ore more elements for promoting adhesion of electrodes to the first insulation layer and then the plurality of electrodes. In an exemplary aspect, titanium (Ti) and titanium dioxide ($TiO_2$) can be the one or more elements for promoting adhesion of electrodes, and the plurality of electrodes can comprise gold.

In still another aspect, the method of producing the electrophysiological recording device can comprise preparing one or more patterns for the plurality of electrodes and the first and/or second insulation layers. It is contemplated that the patterns of the electrodes and insulation layers can be designed using known software, such as, for example and without limitation, L-Edit CAD software. The pattern designs for the electrodes and insulator layers can be printed out on a glass plate, such as, for example and without limitation, a 5 inch (12.7 cm) square glass plate, to thereby form one or more masks. Exemplary pattern designs for the electrodes and insulation layers are respectively shown in FIGS. 6G-6H. Each mask can be oven-baked, cooled, and then placed in a glass container. In an exemplary aspect, each mask can be oven-baked at 115° C. for about 20 minutes, then cooled for about 2-3 minutes, and then placed in a glass container. In a further aspect, a photoresist developer can be applied over the one or more masks for a predetermined amount of time. In an exemplary aspect, AZ 300 MIF (AZ Electronic Materials) can be poured slowly to cover the one or more masks and left for about 10 seconds, at which point the one or more masks can be removed and washed in DI water. In another exemplary aspect, the one or more masks can be dipped in Cr 14-S chromium etch or other suitable composition until the mask becomes transparent, leaving behind the pattern on the glass plate. The one or more masks can then be washed in DI water and dried.

In still another aspect, and with reference to FIG. 6I, the method of producing the electrophysiological recording device can comprise patterning the plurality of electrodes using lithographic techniques. In this aspect, the wafer can be spin coated with photoresist, such as, for example and without limitation, Shipli 1813. In an exemplary aspect, the photoresist can be applied at about 3,000 rpm for about 10 seconds and then baked at about 90° C. for about 6 minutes. In an additional aspect, the photoresist layer can be exposed to Ultra Violet (UV) light through the mask. In this aspect, the wafer can be washed in developer 352 solution or other suitable solution until the exposed photoresist dissolves. The wafer with the remaining photoresist pattern can be washed in DI water, dried, post baked and again exposed to UV light. In a further aspect, the wafer can then be washed in $KI/I_2$ solution to remove the uncovered electrodes. The wafer can then be washed in DI water, dipped in Buffered Oxide Etch (BOE) solution, and again washed in DI water. It is contemplated that the BOE solution can be used to selectively etch the titanium and titanium dioxide layers as described herein. After the electrodes are patterned, the wafer can be washed in developer 352 or other suitable solution to remove the remaining patterned photoresist.

As shown in FIG. 6J, in still another aspect, the method of producing the electrophysiological recording device can comprise applying the second insulation layer thereon the plurality of electrodes and the first insulation layer as described herein.

In yet another aspect, the first and second insulation layers can both be patterned using lithographic techniques. The techniques used to pattern the insulation layers are substantially the same as those used to pattern the plurality of electrodes, as described herein. However, it is contemplated that the patterning of the insulation layers can be done using a different mask. It is further contemplated that the patterning of the second insulation layer can require an additional step of aligning the second insulation layer with the existing pattern defined by the electrodes thereon the wafer. In one aspect, after an insulation layer is properly aligned, the photoresist layer can be exposed to UV light, washed in developer 352 or other suitable solution to dissolve the exposed photoresist, rinsed in DI water, and then dried. In a further aspect, the wafer can then be etched through an anisotropic, reactive ion etching (RIE) process to remove the uncovered portions of the insulation layers, leaving behind the final patterns of the insulation layers. In an exemplary aspect, the wafer can be etched through an RIE process in a Plasmalab 80 system for about 7 minutes to remove the uncovered portions of the insulation layers. FIG. 6K shows the wafer following etching of the second insulation layer.

In another aspect, the method of producing the electrophysiological recording device can comprise soaking the wafer in AZ400K solution or other suitable solution with gentle stirring to peel off the newly formed electrophysiological recording device from the rigid substrate, as depicted in FIG. 6L. In this aspect, it is contemplated that, after the electrophysiological recording device was removed, it can be washed in DI water and then dried. In a further aspect, prior to cell culture, the electrophysiological recording device can be washed with PBS and ethanol and then autoclaved so as to achieve sterilization.

The Housing

Also disclosed is a housing 300 defining a cell culture chamber 340. In exemplary aspects, it is contemplated that at least a portion of the recording portion 220 of the porous membrane 210 can be mountable within the cell culture chamber 340 of the housing 300. In one aspect, and with reference to FIGS. 1-3, the housing 300 can comprise a first base support portion 310 and a second base support portion 320. In this aspect, it is contemplated that the first base support portion 310 can be configured to support the first and second cell culture regions 316 of the porous membrane 210, while the second base support portion 320 can be configured to support the contact portion 318 of the porous membrane. It is further contemplated that the first and second base support portions 310, 320 can be shaped to permit the porous membrane 210 to lie substantially flat on the first base support portion 310 to thereby permit cell culturing on either of the opposed first and second cell culture regions 216 of the porous membrane.

In another aspect, the first base support portion 310 can define an opening 312. In this aspect, it is contemplated that the second base support portion 320 can be configured to support the porous membrane 210 such that at least a portion of the recording portion 220 of the porous membrane overlies the opening 312 of the first base support portion 310. It is further contemplated that the first base support portion 310 can comprise a depressed region 314 that is configured to receive at least a portion of the porous membrane 210, such as, for example and without limitation, the opposed first and second cell culture regions 316 of the porous membrane. In an exemplary aspect, the first base support portion 310 can comprise a depressed region 314 that is depressed by about 10 μm from a top surface of the first base support portion. In this aspect, the size and shape of the depressed region 314 can substantially correspond to the size and shape of a select portion of the porous membrane 210.

Figure 2A:
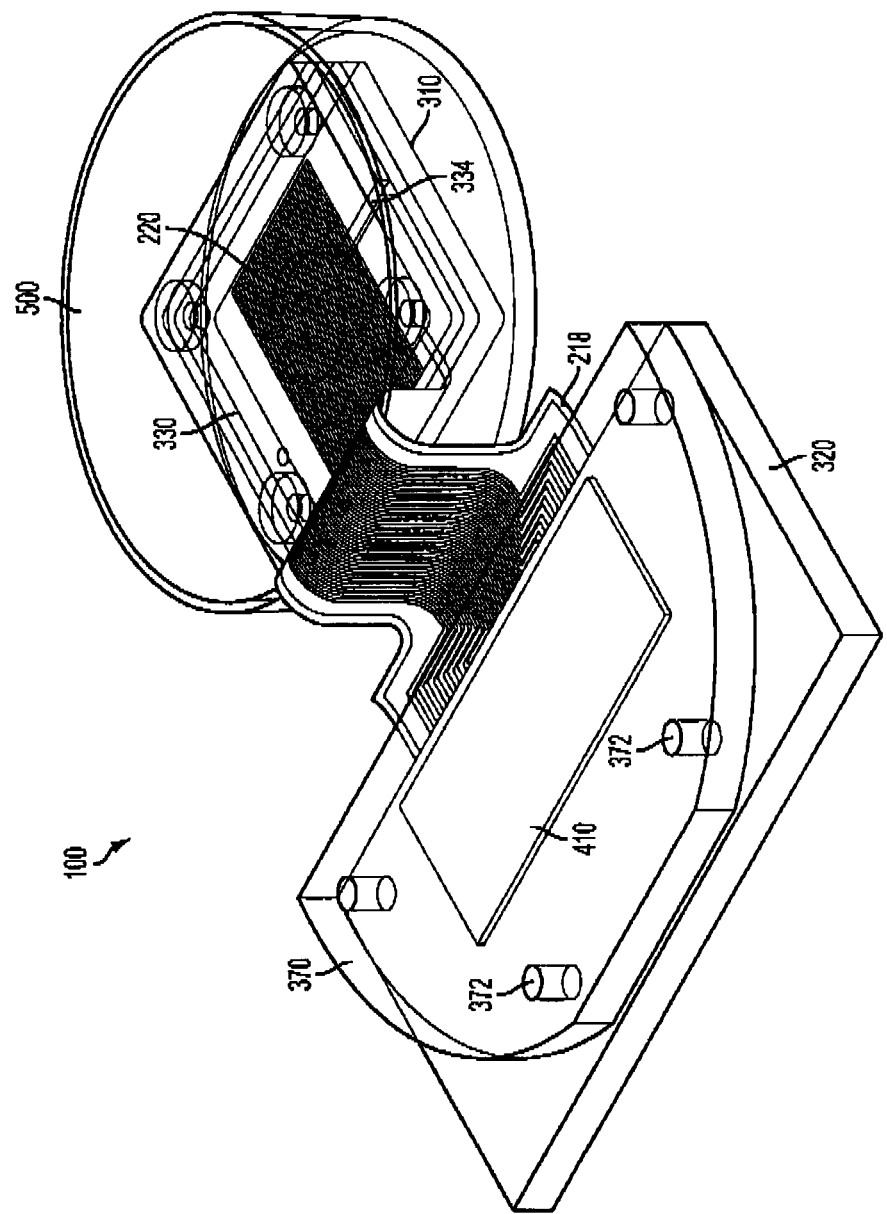
FIG. 2A is a perspective view of the exemplary electrophysiological recording system.
Figure 2B:
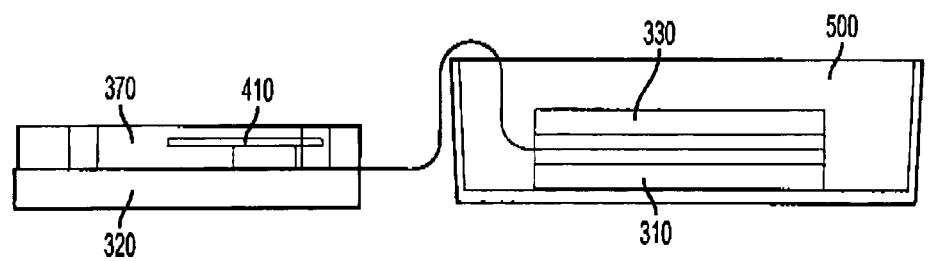
FIG. 2B is a partially transparent side view of the housing of the electrophysiological recording system of FIG. 2A.
Figure 2C:
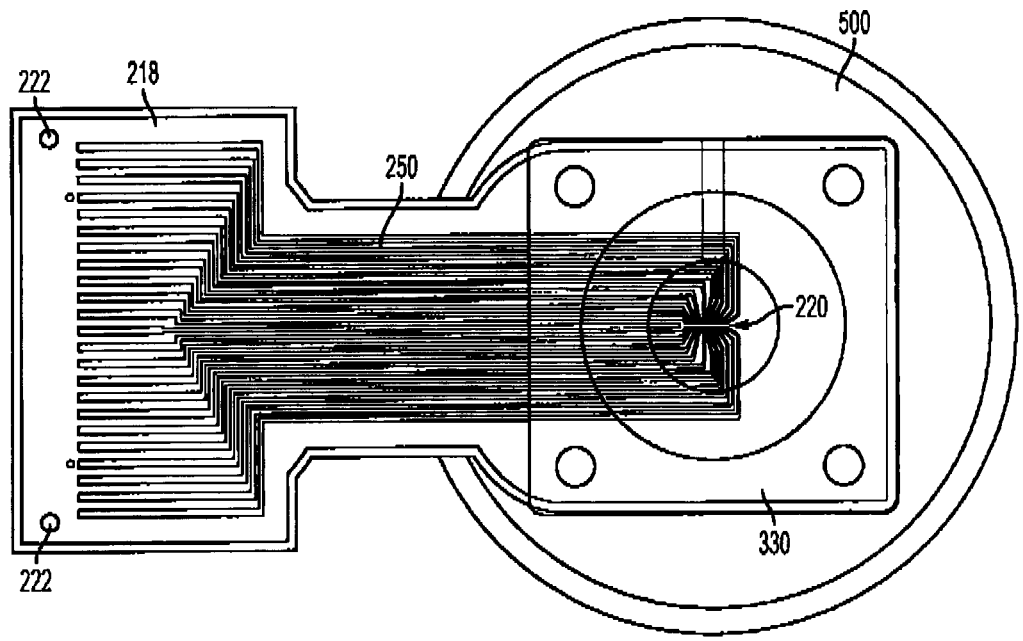
FIG. 2C is a partially transparent top view of the electrophysiological recording system of FIG. 2A.

Optionally, in another aspect, the first base support portion 310 and the second base support portion 320 can be of unitary construction. Alternatively, in still another aspect, as shown in FIGS. 2A-2C, the first base support portion 310 and the second base support portion 320 can be separate pieces of the housing 300. In this aspect, it is contemplated that the first base support portion 310 can be configured for receipt within a conventional cell culture environment, such as, for example and without limitation, a Petri dish, while the second base support portion 320 can be positioned outside the cell culture environment. It is further contemplated that the design of the disclosed housing 300 can permit sterile culturing of cells on the porous membrane 210 in close proximity to computers and other data acquisition equipment 400.

In a further aspect, the first base support portion 310 can define at least one channel 316 in communication with the opening 312. In this aspect, it is contemplated that the at least one channel 316 can permit access to the opening 312, and thus, the porous membrane 210, from a side edge of the first base support portion 310. It is further contemplated that, during culturing, the at least one channel 316 can permit movement and/or circulation of culture media. In still another aspect, the first base support portion 310 and the second base support portion 320 can each comprise a biocompatible polymer. For example, in a non-limiting aspect, it is contemplated that the first base support portion 310 and the second base support portion 320 can each comprise polychlorotrifluoroethylene (PCTFE).

In an additional aspect, the housing can comprise a first cover portion 330. In this aspect, the first cover portion 330 can define an opening 332. In a further aspect, the first cover portion 330 can be configured for attachment thereto the first base support portion 310 such that the opening 332 of the first cover portion is substantially aligned with the opening 312 of the first base support portion 310. In this aspect, it is contemplated that the openings 312, 332 of the first base support portion 310 and the first cover portion 330 can cooperate to define the cell culture chamber 340 for culturing a first group of cells on the top surface 212 of the porous membrane 210 and a second group of cells on the bottom surface 214 of the porous membrane. It is further contemplated that, in use, the opening 332 of the first cover portion 330 can permit access to the top surface 212 of the porous membrane 210 from above the porous membrane, while the opening 312 of the first base support portion 310 can permit access to the bottom surface 214 of the porous membrane from below the porous membrane. It is still further contemplated that the opening 332 of the first cover portion 330 can permit imaging equipment to access the porous membrane 210 for analysis of cellular interactions within the cell culture chamber 340.

Figure 3A:
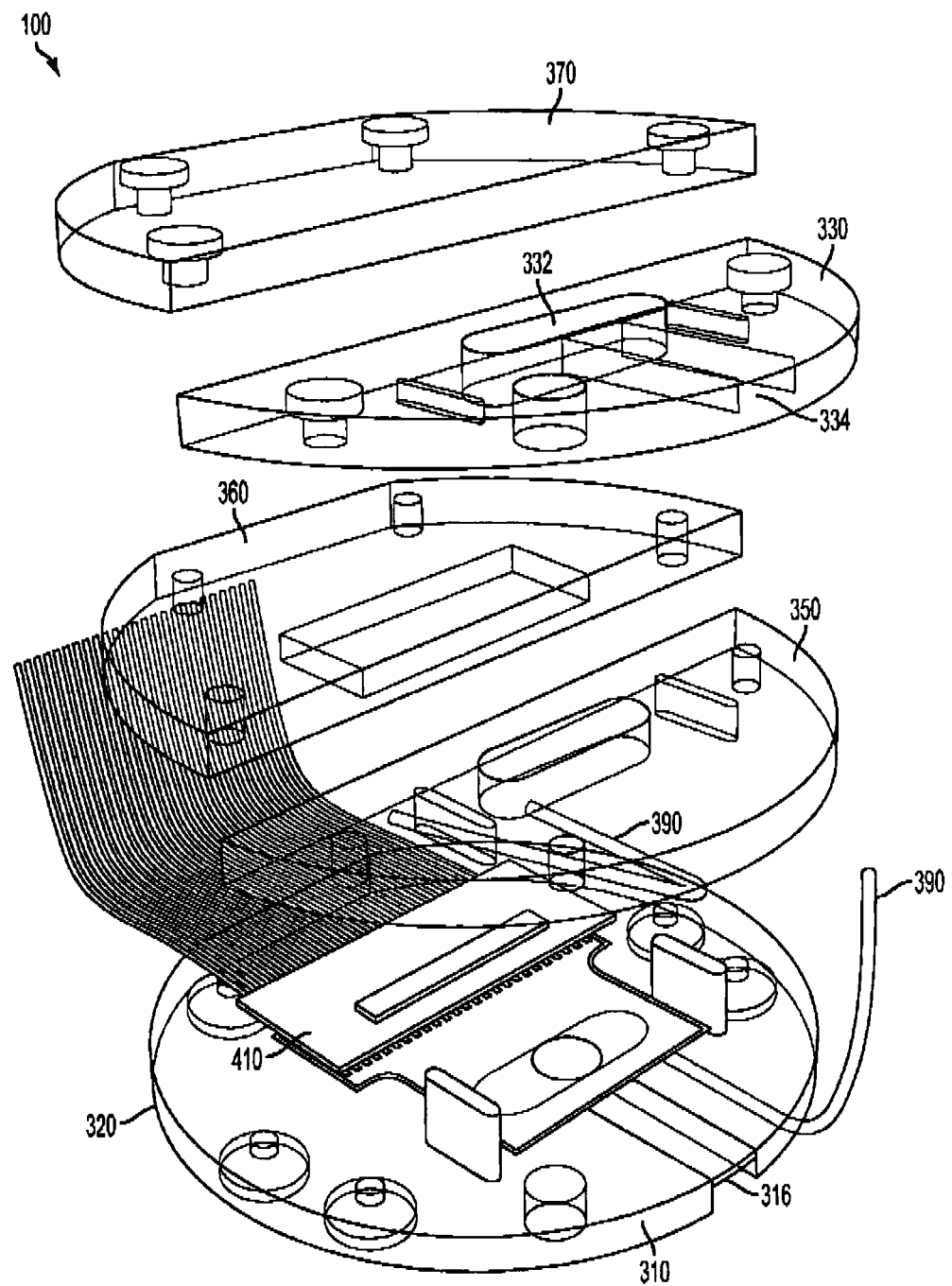
FIG. 3A is an exploded view of the exemplary electrophysiological recording system.
Figure 3B:
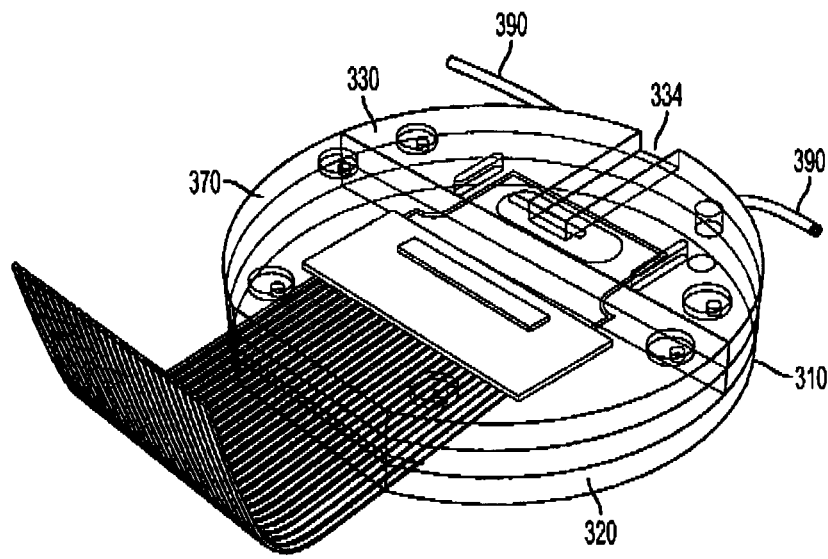
FIG. 3B is a perspective view of the electrophysiological recording system of FIG. 3A, in an assembled configuration.
Figure 3C:
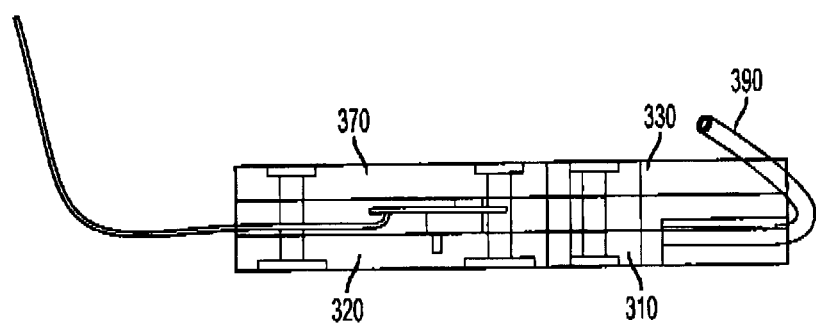
FIG. 3C is a partially transparent side perspective view of the electrophysiological recording system of FIG. 3A.
Figure 3D:
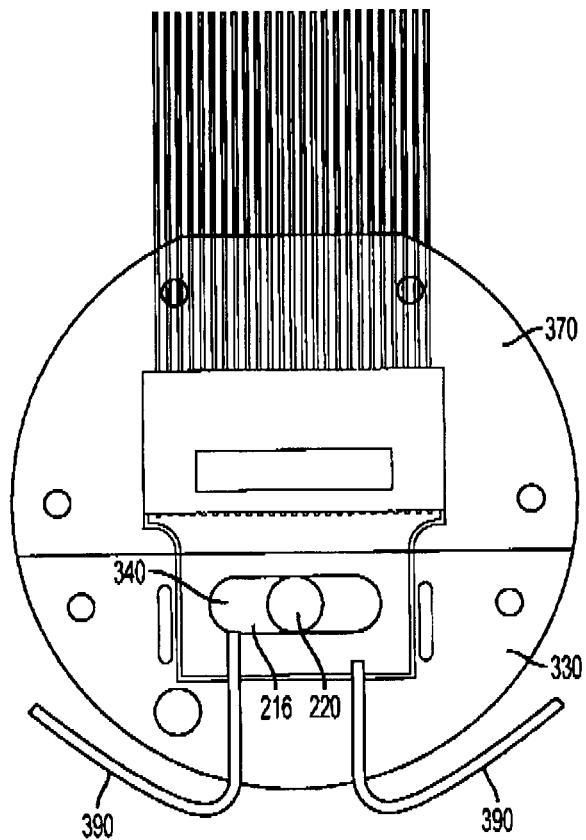
FIG. 3D is a partially transparent top view of the electrophysiological recording system of FIG. 3A.
Figure 3E:
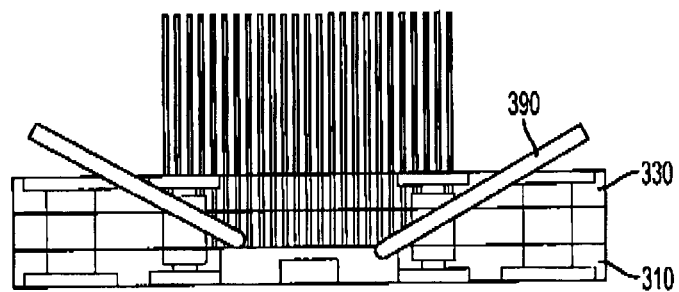
FIG. 3E is a partially transparent front view of the electrophysiological recording system of FIG. 3A.

Optionally, in one aspect, and as shown in FIG. 3A, the cell culture chamber 340 can be surrounded by a sealant layer 350 for preventing leakage of cells or culture media from the cell culture chamber. In this aspect, it is contemplated that the sealant layer 350 can comprise an elastomer, such as, for example and without limitation, a fast-curing silicone elastomer. For example, in a non-limiting aspect, the sealant layer 350 can comprise SYLGARD™ silicone elastomer manufactured by DOW CORNING.

In another aspect, the first cover portion 330 can define at least one channel 334 in communication with the opening 332. In this aspect, it is contemplated that the at least one channel 334 can permit access to the opening 332, and thus, the porous membrane 210, from a side edge of the first cover portion 330. It is further contemplated that, during culturing, the at least one channel 334 can permit movement and/or circulation of culture media. In an additional aspect, the first cover portion 330 can be selectively removable from the housing 300. In a further aspect, the first cover portion 330 can comprise a biocompatible polymer. For example, in a non-limiting aspect, it is contemplated that the first cover portion 330 can comprise polychlorotrifluoroethylene (PCTFE).

In still another aspect, as shown in FIG. 1, the housing 300 can optionally comprise an intermediate support plate 360. In this aspect, the intermediate support plate 360 can be configured for operative coupling to the contact portion 218 of the porous membrane 210. It is contemplated that the intermediate support plate 360 can be integrally connected with a one-piece electrical connector 410 as described herein for operative connection to the contact ends 256 of the plurality of electrodes 250 within the contact portion 218 of the porous membrane 210. In an additional aspect, the intermediate support plate 360 can be configured for attachment thereto the second base support portion 320.

In an exemplary aspect, the intermediate support plate 360 can optionally comprise a gasket 362 configured to surround the contact ends 256 of the plurality of electrodes 250 and the one-piece electrical connector 410 within the contact portion 218 of the porous membrane 210. In this aspect, it is contemplated that the gasket 362 can cooperate with the housing 300 to protect the contact ends 256 of the plurality of electrodes 250 and the one-piece electrical connector 410 from moisture within the housing, thereby preventing short circuits and signal duplication. In one aspect, the intermediate support plate 360 can comprise an elastomer, such as, for example and without limitation, a fast-curing silicone elastomer. For example, in a non-limiting aspect, the intermediate support plate 360 can comprise SYLGARD™ silicone elastomer manufactured by DOW CORNING. It is contemplated that, when the housing 300 does not comprise an intermediate support plate 360, the gasket 362 and the electrical connector 410 can be arranged directly thereon the second base support portion of the housing.

In a further aspect, the housing 300 can further comprise a second cover portion 370. In this aspect, the second cover portion 370 can be configured to overlie the second base support portion 320 of the housing.

In another aspect, it is contemplated that the first base support portion 310 and the first cover portion 330, as well as the second base support portion 320 and the second cover portion 370, can each have one or more corresponding alignment holes 372. In this aspect, it is further contemplated that, in an operative position, the corresponding alignment holes 372 of the first base support portion 310 and the first cover portion 330 are substantially axially aligned, and the second base support portion 320 and the second cover portion 370 are substantially axially aligned. In an exemplary aspect, the corresponding alignment holes 372 of the first base support portion 310 and the first cover portion 330 can be configured to receive a fastener such that the first base support portion and the first cover portion are secured to one another, and the corresponding alignment holes of the second base support portion 320 and the second cover portion 370 can be configured to receive a fastener such that the second base support portion and the second cover portion are secured to one another. When the housing 300 comprises an intermediate support plate 360, it is still further contemplated that the intermediate support plate 360 can have alignment holes 372 that are aligned with corresponding alignment holes of the second base support portion 320 and the second cover portion 370 when the housing is placed in the operative position. In an exemplary aspect, the alignment holes 372 of the intermediate support plate 360 can be configured to receive a fastener such that the second base support portion 320, the intermediate support plate, and the second cover portion 370 of the housing 300 can be secured to one another. In another exemplary aspect, it is contemplated that the fasteners used to secure the first base support portion 310 to the first cover portion 330 and to secure the second base support portion 320, the intermediate support plate 360, and the second cover portion 370 of the housing 300 can be screws, such as for example and without limitation, nylon screws. Optionally, in another aspect, the second cover portion 370 can be integrally formed with the intermediate support plate 360. In other exemplary aspects, it is contemplated that the first base support portion 310 can be secured to the first cover portion 330 using any known method or technique. Similarly, it is contemplated that the second base support portion 320, the intermediate support plate 360, and the second cover portion 370 can be secured to one another using any known method or technique.

Figure 8:
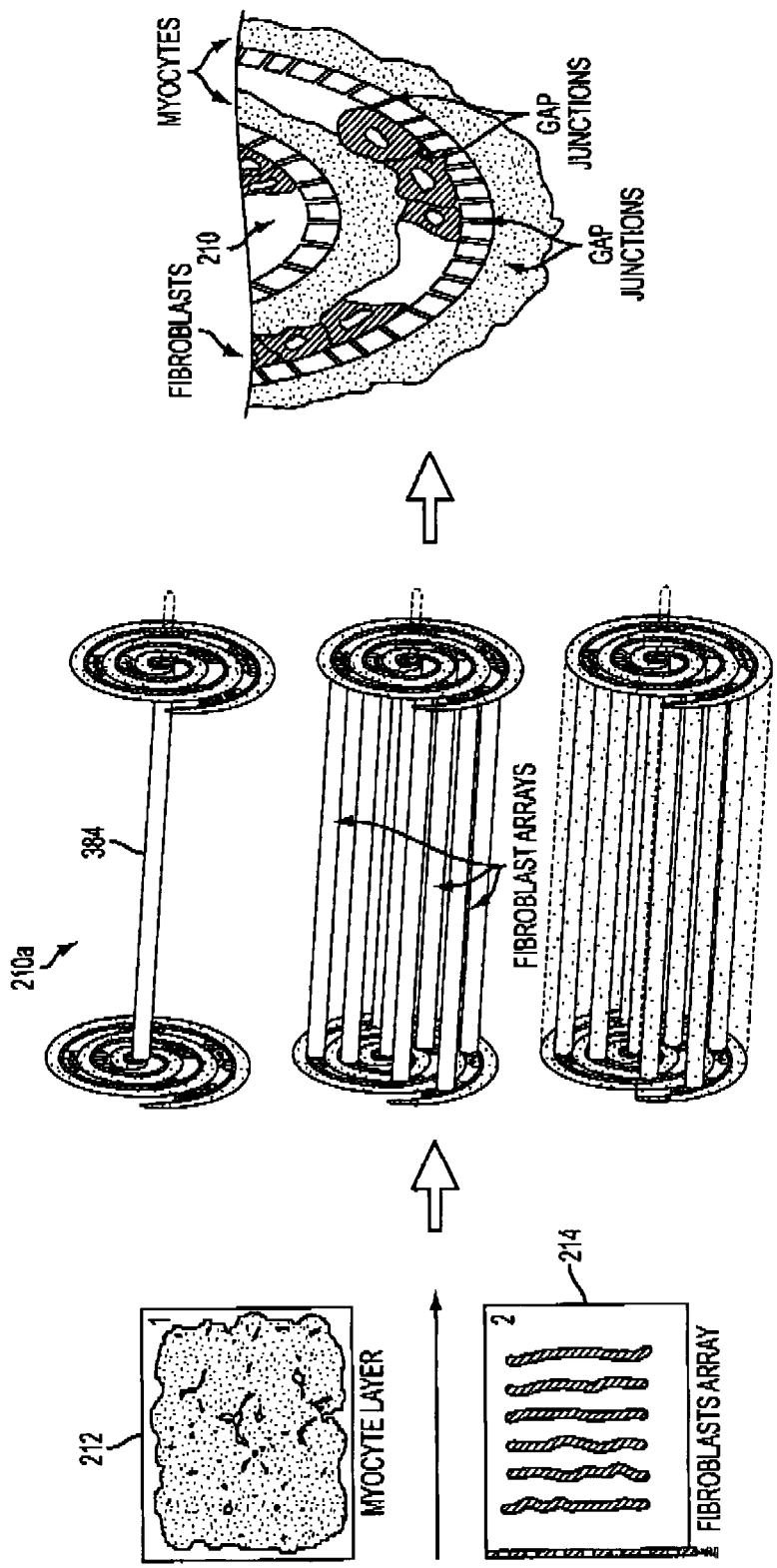
FIG. 8 displays an exemplary process for forming a three-dimensional cell culture, as described herein. In particular.
Figure 9:
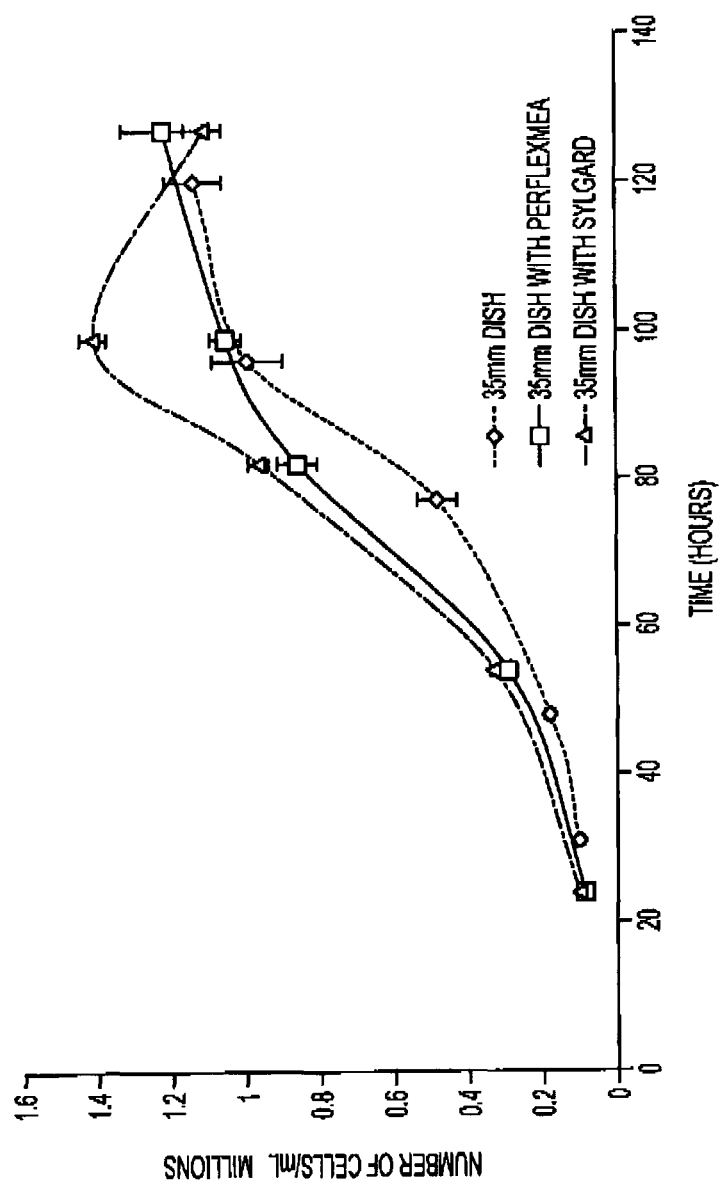
FIG. 9 displays a graph of the growth rate of cells cultured in Petri dishes in which either a porous membrane as described herein or pieces of Sylgard were added to the culture medium, as compared to the growth rate of cells cultured alone in a Petri dish.

In various aspects, and with reference to FIGS. 1 and 8, the electrophysiological recording system 100 can further comprise means for rolling up the porous membrane 210 to form a three-dimensional cell culture 210a. In these aspects, it is contemplated that the means for rolling up the porous membrane 210 can be configured to prevent wobbling, compression, and/or over-stretching of the porous membrane during formation of the three-dimensional cell culture 210a. In one aspect, the means for rolling up the porous membrane 210 can be integrated into the housing 300. Alternatively, it is contemplated that the means for rolling up the porous membrane 210 can be an isolated component of the electrophysiological recording system 100.

In exemplary aspects, it is contemplated that the three-dimensional cell culture 210a can have a substantially spiral cross-sectional shape, as shown in FIG. 8. However, it is contemplated that the three-dimensional cell culture 210a can have any desired three-dimensional shape. It is further contemplated that the three-dimensional cell culture 210a can permit cells cultured on the opposed top and bottom surfaces 212, 214 of the porous membrane 210 to communicate either through the porous membrane or through direct contact among the various layers of the three-dimensional cell culture.

In one aspect, the means for rolling up the porous membrane 210 can comprise a gear assembly 380. In this aspect, the gear assembly 380 can comprise a rod 384 configured for attachment to at least a portion of the recording portion 220 of the porous membrane 210. In another aspect, the gear assembly 380 can comprise at least one gear 382 operatively coupled to the rod 384 and rotatable about a rotation axis RA. In this aspect, it is contemplated that rotation of the at least one gear 382 can result in a corresponding rotation of the rod 384. It is contemplated that each gear 382 of the at least one gear can have a diameter of about 1 mm. In this aspect, it is contemplated that the porous membrane 210 can be glued or otherwise attached to the rod 384 such that rotation of the rod causes a corresponding rotation (and roll-up) of the porous membrane. In an additional aspect, the rod 384 can be configured an electrode 386 configured for measurement of electrical properties of the three-dimensional cell culture 210a. In this aspect, it is contemplated that the electrode 386 of the rod 384 can be further configured for electrical communication with the data acquisition equipment 400. It is further contemplated that the porous membrane 210 can be analyzed sequentially in its two-dimensional structure by the plurality of electrodes 250 of the electrophysiological recording device 200 and in its three-dimensional structure 210a by the plurality of electrodes 250 and/or the electrode 386 of the rod 384. In an exemplary aspect, the electrode 386 of the rod 384 can be an ion-selective electrode, such as, for example and without limitation, an electrode that is selective for potassium ($K^+$) ions.

In another aspect, and as shown in FIG. 1, when the means for rolling up the porous membrane 210 is integrated into the housing 300, it is contemplated that the at least one gear 382 of the gear assembly 380 can comprise a first gear 382a and a second gear 382b. In this aspect, the means for rolling up the porous membrane 210 can further comprise a first groove 318a and a second groove 318b defined within at least the first base support portion 310. Optionally, the first groove 318a and the second groove 318b can extend into, and be further defined by, the first cover portion 330. It is contemplated that the first groove 318a can be configured for receipt of the first gear 382a and that the second groove 318b can be configured for receipt of the second gear 382b. It is further contemplated that the first groove 318a can be spaced apart from the second groove 318b along the common rotation axis RA of the first and second gears 382a, 382b. In a further aspect, the first groove 318a and the second groove 318b can be positioned on opposed sides of the opening 312 of the first base support portion 310.

Figure 1E:
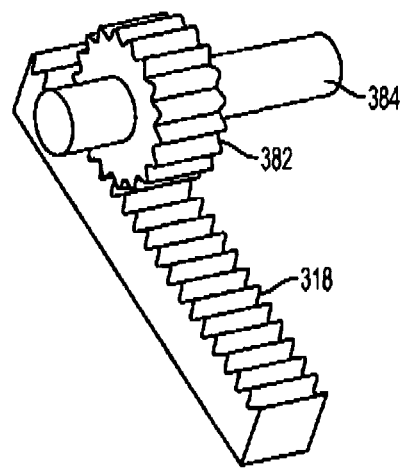
FIG. 1E is a perspective view of a gear assembly of the electrophysiological recording system of FIG. 1A.

In still another aspect, the first groove 318a and the second groove 318b can be inclined at a predetermined angle. In this aspect, it is contemplated that the predetermined angle can range from about 1 degree to about 10 degrees and more preferably, from about 2 to about 3 degrees. It is further contemplated that the incline of the first and second grooves 318a, 318b, as well as the diameter of the at least one gear 382, can determine the space between the various layers of the porous membrane 210 within the three-dimensional cell culture 210a. In exemplary aspects, it is contemplated that the space between the various layers of the porous membrane 210 can range from about 1 to about 20 µm, and more preferably from about 5 to about 10 µm. In a further aspect, it is contemplated that the first groove 318a and second groove 318b can define a surface configured for complementary engagement with the at least one gear 382, such as, for example and without limitation, a surface shaped to conform to teeth of the at least one gear, as shown in FIG. 1E.

In still another aspect, the rod 384 of the gear assembly 380 can comprise stainless steel. In this aspect, it is contemplated that the rod 384 can be a stainless steel needle, such as a stainless steel needle having a diameter ranging from about 50 to about 150 µm, and more preferably from about 80 to about 120 µm. In a further aspect, the electrode 386 of the rod 384 can be glued or otherwise secured along the length of the rod, and one or more connectors can be secured to the rod for communication with the data acquisition equipment 400. Optionally, in one aspect, the rod 384 can be insulated with parylene or another known polymer for creating a moisture and dielectric barrier around the rod.

Figure 1F:
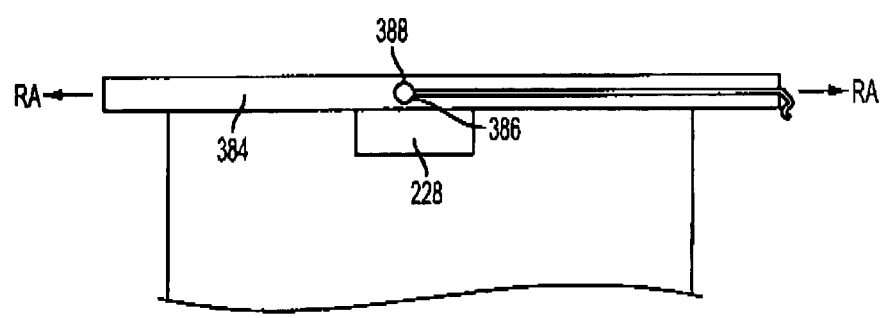
FIG. 1F is a side view of a rod of a gear assembly and a porous membrane having a central aperture, as described herein.

In another aspect, it is contemplated that a tip 388 of the electrode 386 of the rod 384 can be located at a center portion of the rod and coated with a suitable resin. For example, and without limitation, it is contemplated that the resin used to coat the tip 388 of the electrode 386 can be any known liquid ion-exchange resin that can be cationic or anionic, depending on the particular ion to be quantified, inside a polymer-based substrate, including those manufactured by Fluka (Sigma). In an additional aspect, it is contemplated that the porous membrane 210 can be glued or otherwise attached to the rod 384 before cells are cultured on the porous membrane. Optionally, in still another aspect, as shown in FIG. 1F, the porous membrane 210 can define a central aperture 228 that is substantially aligned with the tip 388 of the electrode 386 of the rod 384 such that electrolyte diffusion is promoted within the three-dimensional cell culture 210a. In another aspect, the central aperture 228 can have a length in a direction substantially perpendicular to the rotation axis RA of the gear assembly 380. In this aspect, the length of the central aperture 228 can range from about 150 µm to about 250 µm and, more preferably, can be about 200 µm.

Optionally, in an additional aspect, the housing 300 can further comprise at least one air suction tube 390 for removing air bubbles from the cell culture chamber 340. In this aspect, it is contemplated that the at least one air suction tube 390 can comprise a first suction tube 390a positioned below the porous membrane 210 and a second suction tube 390b positioned above the porous membrane. It is further contemplated that the at least one air suction tube 390 can be received within corresponding bores 392 defined therein the first cover portion 330 and/or the first base support portion 310 of the housing 300 such that the at least one air suction tube is positioned proximate the porous membrane 210.

In additional exemplary aspects, it is contemplated that the materials of the housing 300 can be configured to withstand temperatures up to at least 200° C. such that the various elements of the housing can be autoclaved between uses. It is further contemplated that the materials of the housing 300 can be configured to withstand conventional laboratory sterilization treatments with alcohol and other known agents.

In exemplary aspects, the electrophysiological recording system can further comprise a Petri dish 500. In these aspects, it is contemplated that the cell culture chamber 340 of the housing 300 can be configured for receipt therein the Petri dish 500. More particularly, in an exemplary aspect, it is contemplated that the first base support portion 310 and the first cover portion 330 of the housing 300 can be shaped for receipt therein the Petri dish 500. It is further contemplated that, when the Petri dish 500 contains cell culture media, the first base support portion 310, which supports the porous membrane 210, and the first cover portion 330 of the housing can be configured for receipt therein the Petri dish 500 such that the cell culture media contacts the opposed first and second cell culture regions 216 of the porous membrane. It one aspect, the Petri dish 500 can be a conventional Petri dish manufactured from glass or plastic, including, for example and without limitation, a conventional 60 mm-diameter Petri dish.

Data Acquisition Equipment

In a further aspect, the electrophysiological recording system 100 can further comprise data acquisition equipment 400. In this aspect, as described herein, the data acquisition equipment 400 can be placed in operative electrical communication with the contact ends 256 of the plurality of electrodes 250 and/or with the electrode 386 of the gear assembly 380 using any known electrical communication means. As described herein, the data acquisition equipment 400 can comprise a one-piece electrical connector 410 for connection to the contact ends 256 of the plurality of electrodes 250. It is contemplated that the data acquisition equipment 400 can further comprise additional connectors for connection to the electrode 386 of the gear assembly 380.

In another aspect, the data acquisition equipment 400 can further comprise a signal amplification and recording subsystem, a temperature control subsystem, noise reduction subsystem, and a computer-user interface. Generally, in this aspect, the signal amplification and recording subsystem can be configured to amplify the signals recorded by the plurality of electrodes 250 to permit detailed analysis of the signal deflections, the temperature control subsystem can be configured to maintain the temperature of the cell culture chamber 340, the noise reduction subsystem can be configured to insulate and minimize signal noise from the environment surrounding the cell culture chamber, and the computer-user interface can be configured to collect and visualize the electrical signals generated by the cells cultured on the porous membrane 210. It is contemplated that the housing 300 of the electrophysiological recording system 100 can comprise openings in appropriate locations to permit electrical connection between the electrodes 250 of the electrophysiological recording system and the data acquisition equipment 400. Thus, for example, it is contemplated that an opening within the second cover portion 370 (or, alternatively, defined by the second cover portion and the second base support portion 320) can permit connection of conventional cables or wires between a single-piece electrical connector 410 (coupled to the contact ends 256 of the plurality of electrodes 250) and external data acquisition equipment 400.

In an additional aspect, the signal amplification and recording subsystem can comprise a known data acquisition system, such as, for example and without limitation, a MEA60 amplifier system. In a further aspect, the signal amplification and recording subsystem can be configured to have a gain control mechanism. In this aspect, it is contemplated that the gain control mechanism can comprise means for automatically adjusting gain values according to the measured signal magnitude and noise. In still another aspect, the signal amplification and recording subsystem can be configured for connection to the contact ends 256 of the plurality of electrodes 250 through a single-piece interface connector 410 or other connection means. In yet another aspect, the signal amplification and recording subsystem can be configured for connection to the computer-user interface. In this aspect, it is contemplated that the signal amplification and recording subsystem can be configured for connection to the computer-user interface using a known matrix cable system (MCS). In an exemplary aspect, the signal amplification and recording subsystem can comprise a general ground connected to the signal amplification and recording subsystem for electrically grounding the overall electrophysiological recording system. In this aspect, it is contemplated that the general ground can be, for example and without limitation, a chloridized silver wire that is immersed in cell culture media.

In still another aspect, the temperature control subsystem can comprise an incubator, including for example and without limitation, a heating/cooling micro-incubator stage (HC-MIS) incubator, such as, for example and without limitation, a PTC-10 (Peltier Temperature Control) system. It is contemplated that the incubator of the temperature control subsystem can be configured to maintain the porous membrane 210 at a temperature ranging from about 37° C. to about 38° C. It is further contemplated that any known temperature control mechanism can be used for purposes of the disclosed electrophysiological recording system 100. In exemplary aspects, it is contemplated that the temperature control subsystem can be positioned within the housing 300 of the disclosed electrophysiological recording system 100.

In yet another aspect, the noise reduction subsystem can comprise a Faraday cage for receiving the electrophysiological recording device and housing. In an exemplary aspect, the Faraday cage can comprise a box having inner walls coated with aluminum mesh. It is contemplated that the Faraday cage can be configured to increase shielding against stray noise from the outside environment. In an additional aspect, when the electrophysiological recording system 100 comprises a Petri dish 500, the noise reduction subsystem can further comprise an aluminum foil layer for shielding the Petri dish, thereby minimizing electromagnetic noise in the recorded signal.

In a further aspect, the computer-user interface can comprise a computer having a processor and a memory and a user-input means. In this aspect, it is contemplated that the computer-user interface can comprise a keyboard or other means for inputting information to the computer. It is further contemplated that the processor of the computer can be configured to perform steps required for observation and storage of the signals recorded from the electrodes 250 of the electrophysiological recording device 200 and/or gear assembly 380. It is still further contemplated that the memory of the computer can store conventional software for instructing the processor to observe and store the recorded signals. In an exemplary aspect, the memory can store conventional data acquisition software, such as, for example and without limitation, MC Rack software (Multi Channel Systems).

Methods for Analyzing Cells

In use, the electrophysiological recording system described herein can be incorporated into various methods for analyzing cells. In one aspect, a method for analyzing cells can comprise applying a first group of cells thereon the top surface of the porous membrane. In this aspect, it is contemplated that the first group of cells can be applied thereon the first cell culture region. In another aspect, the method for analyzing cells can comprise applying a second group of cells thereon the bottom surface of the porous membrane. In this aspect, it is contemplated that the second group of cells can be applied thereon the second cell culture region. Optionally, the method for analyzing cells can comprise any known methods for optimizing acceptance of cells by the porous membrane. For example, it is contemplated that the method for analyzing cells can further comprise the step of applying one or more physiological substrates, such as, for example and without limitation, collagen, laminin, and the like, to at least one of the top or bottom surfaces of the porous membrane prior to application of the first and second groups of cells.

In exemplary aspects, the first group of cells can be different from the second group of cells. Thus, it is contemplated that the first group of cells can be of a first cell type and the second group of cells can be of a second cell type. In one exemplary aspect, the first group of cells can be cardiac myocytes and the second group of cells can be myofibroblasts or fibroblasts. In this aspect, it is contemplated that analysis of these two groups of cells can be used to study cell-to-cell communication in injured cardiac tissue. In another exemplary aspect, the first and second groups of cells can comprise one or more of neurons, oligodendrocytes, and astrocytes. In this aspect, it is contemplated that analysis of these groups of cells can be used to study communication maps in heterotypical neuronal tissue, as well as the pharmacological relevance of non-neuronal cells to conduction. In an additional exemplary aspect, the first group of cells can comprise smooth muscle cells and the second group of cells can comprise endothelial cells. In this aspect, it is contemplated that analysis of these two groups of cells can be used to study intercellular communication based on different connexins expressed and signal transduction that occurs between the cells as the endothelial cells are stimulated and the muscle cells respond. It is further contemplated that the disclosed method can be used to analyze the pharmacology of lipidimia, as well as arterial agonists and antagonists, by monitoring changes in shape of smooth muscle cells resulting from contraction or relaxation after application of agonists or antagonists to the endothelial cell layer.

In an additional aspect, the method for analyzing cells can comprise positioning the porous membrane in a cell culture medium. In this aspect, when the porous membrane is secured to a housing as described herein, the step of positioning the porous membrane in a cell culture medium can comprise positioning at least the first base support portion of the housing within a container holding a cell culture medium, such as, for example and without limitation, a Petri dish. Alternatively, when the first base support portion and the second base support portion of the housing are of unitary construction as described herein, then the step of positioning the porous membrane in a cell culture medium can comprise positioning at least the first base support portion and the second base support portion of the housing within a container holding a cell culture medium, such as, for example and without limitation, a Petri dish.

In a further aspect, the method for analyzing cells can comprise detecting at least one electrical signal at at least one recording end of the plurality of electrodes of the electrophysiological recording device indicative of one or more electrical properties of the first and second groups of cells. In this aspect, it is contemplated that, when the porous membrane is connected to a plurality of electrodes and first and second insulation layers to form an electrophysiological recording device as described herein, the step of detecting at least one electrical signal can comprise positioning the porous membrane in the cell culture medium such that the recording ends of at least a portion of the electrodes contact the cell culture medium. It is further contemplated that, when the porous membrane is secured within a housing as described herein, the step of detecting at least one electrical signal can comprise positioning the porous membrane such that the recording ends of at least a portion of the electrodes are positioned within the cell culture chamber defined by the first base support portion and the first cover portion of the housing.

In still a further aspect, the method for analyzing cells can comprise transmitting the at least one electrical signal to the data acquisition equipment described herein. In this aspect, it is contemplated that the step of transmitting the at least one electrical signal can comprise electrically connecting the plurality of electrodes of the electrophysiological recording device to data acquisition equipment as described herein. More particularly, it is contemplated that the step of detecting at least one electrical signal can comprise electrically connecting the contact ends of the plurality of electrodes to the data acquisition equipment. For example, and without limitation, the step of detecting at least one electrical signal can comprise electrically connecting an electrical connector as described herein to the contact ends of the plurality of electrodes.

In another aspect, the method for analyzing cells can comprise receiving the at least one electrical signal. In this aspect, it is contemplated that the data acquisition equipment described herein can be configured to receive the at least one electrical signal. In an exemplary aspect, the step of receiving the at least one electrical signal can comprise storing the at least one electrical signal in a memory as described herein. In another exemplary aspect, the step of receiving the at least one electrical signal can comprise processing the at least one electrical signal using software as described herein.

In an additional aspect, the method for analyzing cells can optionally comprise the step of rolling up the porous membrane to form a three-dimensional cell culture. In this aspect, it is contemplated that the above steps of detecting, transmitting, and receiving the at least one electrical signal can be performed while the porous membrane is in a flat configuration and then substantially repeated following formation of the three-dimensional cell culture. Alternatively, the steps of detecting, transmitting, and receiving the at least one electrical signal can be performed only after the three-dimensional cell culture is formed as described herein. Thus, it is contemplated that the disclosed systems and methods can permit controlled culturing of two groups of cells prior to formation of the three-dimensional cell culture. In one aspect, the step of rolling up the porous membrane can comprise attaching at least a portion of the recording portion of the porous membrane to the rod of a gear assembly as described herein. In another aspect, the step of rolling up the porous membrane can comprise rotating the at least one gear of the gear assembly along a rotation axis such that the rod is rotated a corresponding amount, thereby rolling up the porous membrane. It is contemplated that, when the means for rolling up the porous membrane comprises first and second grooves defined within the first base support portion as described herein, the step of rolling up the porous membrane can comprise rotating a first gear along the first groove and a second gear along the second groove. It is further contemplated that the respective first and second gears can be advanced along the respective first and second grooves as the gears are rotated. For example, in an exemplary aspect, the respective first and second gears can be advanced along the respective first and second grooves toward the second base support portion of the housing as the gears are rotated. It is still further contemplated that, when the porous membrane is secured within a housing as described herein, the step of rolling up the porous membrane can comprise removing the first cover portion of the housing prior to rotation of the at least one gear. In exemplary aspects, the rotation of the at least one gear can be done manually until a desired degree of rotation and roll-up of the porous membrane is achieved.

As set forth herein, in various aspects, after formation of the three-dimensional cell culture, the method of analyzing cells can further comprise detecting at least one electrical signal indicative of one or more electrical properties of the first and second groups of cells. In these aspects, it is contemplated that, when the porous membrane is connected to a rod comprising an electrode as described herein, the step of detecting at least one electrical signal can comprise positioning the three-dimensional cell culture in the cell culture medium such that the electrode of the rod contacts the cell culture medium. It is further contemplated that the plurality of electrodes of the electrophysiological recording device can continue to detect the at least one electrical signal following formation of the three-dimensional cell culture. It is further contemplated that, after the three-dimensional cell culture is positioned within the cell culture medium, the method for analyzing cells can comprise transmitting the at least one electrical signal to the data acquisition equipment described herein. In one aspect, it is contemplated that the step of transmitting the at least one electrical signal can comprise electrically connecting the electrode of the rod to data acquisition equipment as described herein. It is still further contemplated that, after the three-dimensional cell culture is positioned within the cell culture medium, the data acquisition equipment can receive the at least one electrical signal in the same manner described herein with respect to the flat configuration of the porous membrane. Thus, it is contemplated that, after the three-dimensional cell culture is positioned within the cell culture medium, the at least one electrical signal can be stored in a memory as described herein and/or can be processed using software as described herein.

In exemplary aspects, it is contemplated that, following culture of the first and second groups of cells as described herein, the electrophysiological recording device, including the porous membrane to which the first and second groups of cells are attached, can be selectively removable from the housing for use in other applications.

In exemplary aspects, it is contemplated that the above-described methods of analyzing cells can be used to evaluate particular tissue compositions for various applications. In one exemplary aspect, the methods can be used to evaluate compositions comprising normal and/or hypertrophied cardiac cells. In another exemplary aspect, the methods can be used to evaluate compositions comprising cells obtained from an ischaemic/injured brain cortex. In an additional exemplary aspect, the methods can be used to evaluate compositions comprising normal and/or hypertrophied arterial tissues. In a further exemplary aspect, the methods can be used to evaluate compositions comprising injured endothelial tissue cells, such as cells obtained from an injured portion of the digestive tract. In still another exemplary aspect, the methods can be used to evaluate compositions comprising pulmonary alveoli. In this aspect, it is contemplated that the tissue composition can be evaluated for formation of independent capillary beds.

In additional exemplary aspects, it is contemplated that the above-described methods of analyzing cells can be used to create a cell-based assay that permits performance of a high-throughput drug screening. In these aspects, it is contemplated that the cell-based assay can comprise a plurality of substantially identical cell culture chambers as described herein can be set in line. Each cell culture chamber can contain substantially identical cellular combinations of cells, such as, for example and without limitation, endothelial and smooth muscle cells. Electrical recordings from each respective cell culture chamber can be used to evaluate changes in input resistance that occur in each cell culture chamber. Each cell culture chamber can be connected to various drug concentrations through known microcirculation systems and methods. Thus, it is contemplated that the disclosed systems and methods can provide time synchrony and homogeneity in analyzing particular drug concentrations in various cell cultures. Additionally, it is contemplated that in the disclosed methods, intercellular communication between the different cell types can be restricted by reducing the number of pores and not changing a cell genome during conventional siRNA or transfection procedures.

In a further exemplary aspect, it is contemplated that bioelectrical impedance measurements of selected groups of cells can be obtained using the disclosed systems and methods. In this aspect, it is contemplated that the plurality of electrodes of the electrophysiological recording system can comprise a large electrode (reference electrode) surrounded by a plurality of smaller electrodes. It is contemplated that bioelectrical impedance measurements can be based on calculating the frequency-dependent electrical impedance of cell-covered electrodes, such as, for example and without limitation, gold electrodes as described herein, along the time course of an experiment to thereby monitor cellular morphological changes in cultured cells. It is contemplated that cultured cells on top of the electrodes can behave as insulating particles that hinder unrestricted current flow from the electrode into cell culture media, thereby increasing the overall electrode impedance. It is contemplated that at certain current frequencies, an applied current can couple through the porous membrane capacitance and cross the cellular layer on trans-cellular pathways. For most frequencies, it is contemplated that this current will bypass the cellular bodies. Along these para-cellular pathways, it is contemplated that the current will travel first through thin tunnels between formed between the porous membrane and the plurality of electrodes. The electrical resistance between cells (Rb) and the resistance between cells and the porous membrane ($\alpha$) can be monitored over time using the above-described system. Through monitoring of these properties, it is contemplated that the contraction properties of various tissue compositions can be measured in vitro. It is contemplated that such contractions can induce cell flattening, thereby contributing to a decrease in Rb and an increase in $\alpha$. It is further contemplated that the pores of the membrane can reduce the effective current that the plurality of electrodes detect. It is contemplated that the porous membrane can be selectively modified to obtain an optimal or desired surface for applying a recording/reference electrode. An exemplary technique for such any analysis is described in Arndt S, Seebach J, Psathaki K, Galla H-J, Wegener J. Bioelectrical impedance assay to monitor changes in cell shape during apoptosis. Biosensors and Bioelectronics 2004; 19:583-94, which disclosure is incorporated herein by reference in its entirety.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

EXAMPLES

Experiment 1

Mouse myocytes were cultured on a first surface of a porous membrane. Tumor cells (HeLa) were cultured on a second surface of the porous membrane. Prior to application of the myocytes to the first surface and the tumor cells to the second surface, both surfaces were coated with a mixture of collagen, laminin and fibronectin. The cultured myocytes beat spontaneously for a week. Recordings from these cells using a disclosed electrophysiological recording system are presented in FIGS. 12A-12D. Lucifer yellow injected in cells at one side of the membrane diffused through gap junctions into cells on the other side, demonstrating functional interaction between the tumor cells and the cardiac myocytes.

Experiment 2

50,000±2500 HeLa WT cells were plated in three sets of five 35 mm Petri dishes each. The first set was used as control. Small 33 mm pieces of the disclosed porous membrane and of Sylgard were placed in the second and third set, respectively. Cell number was calculated everyday from each set using a hemocytometer during the following 5 consecutive days.

Figure 10:
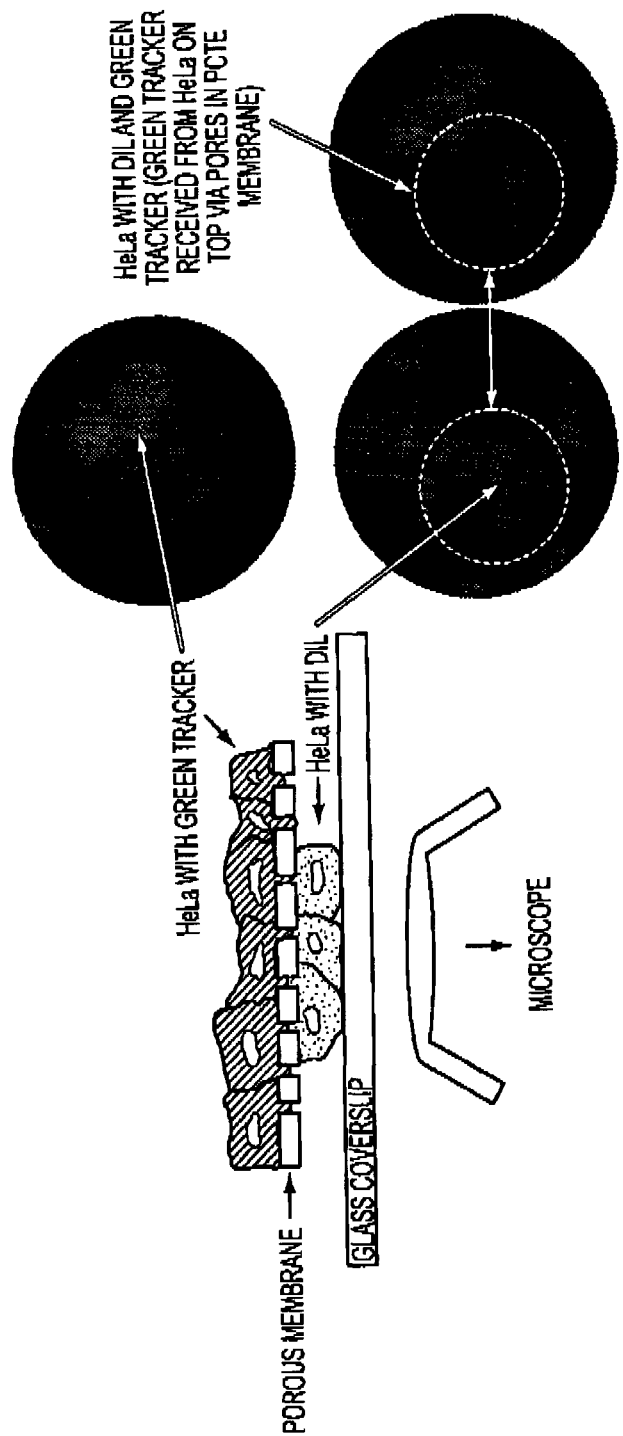
FIG. 10 describes an experiment that was used to confirm cell-to-cell communication through the porous membrane of an exemplary electrophysiological recording device as described herein.
Figure 11A:
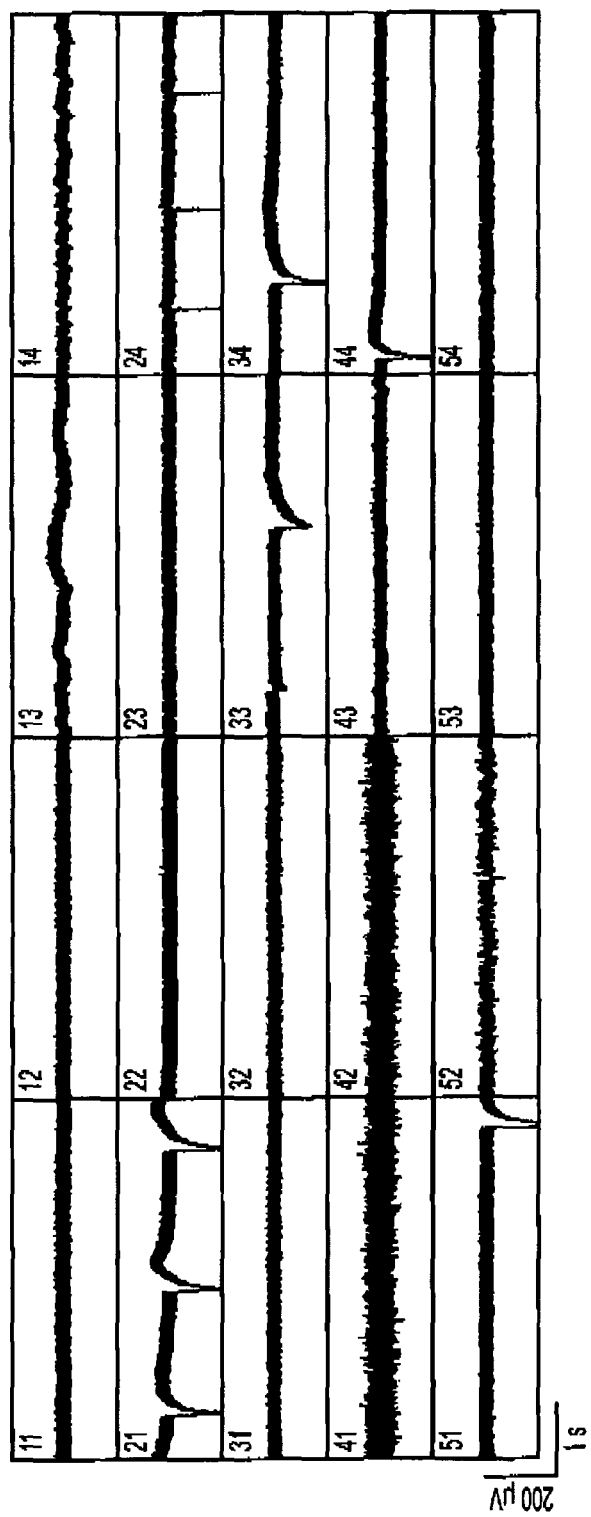
FIG. 11A displays recordings from an electrode array of the electrophysiological recording device.
Figure 11B:
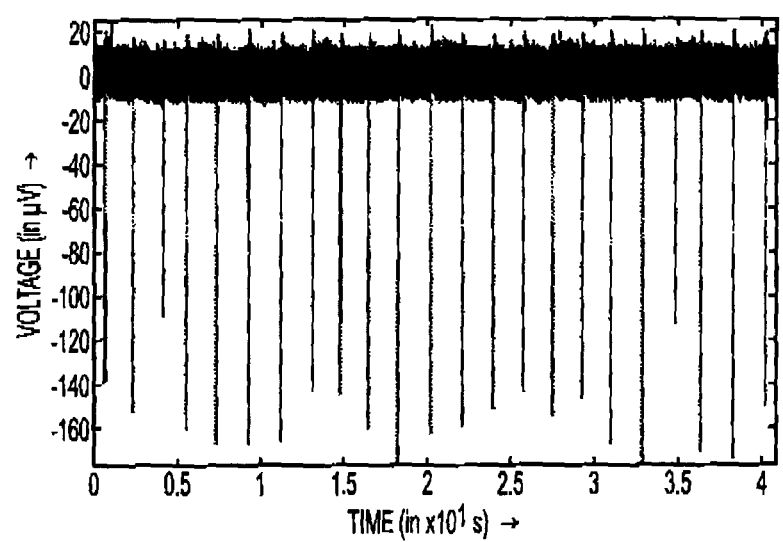
FIG. 11B displays a single electrode recording at a constant beat rate.
Figure 11C:
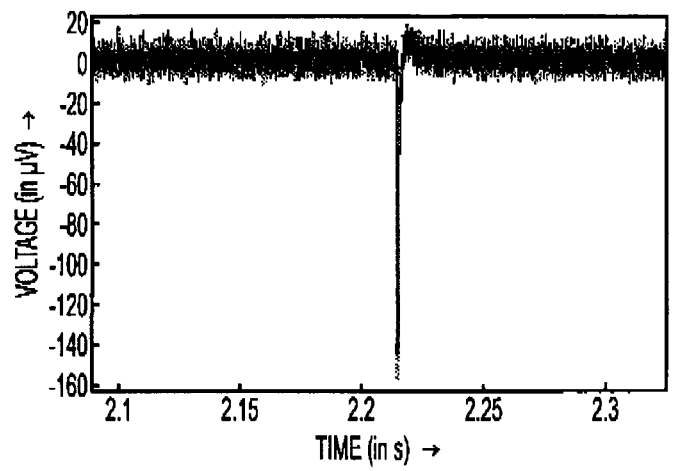
FIG. 11C displays a close-up of an action potential measured by an electrode of the electrode array.
Figure 11D:
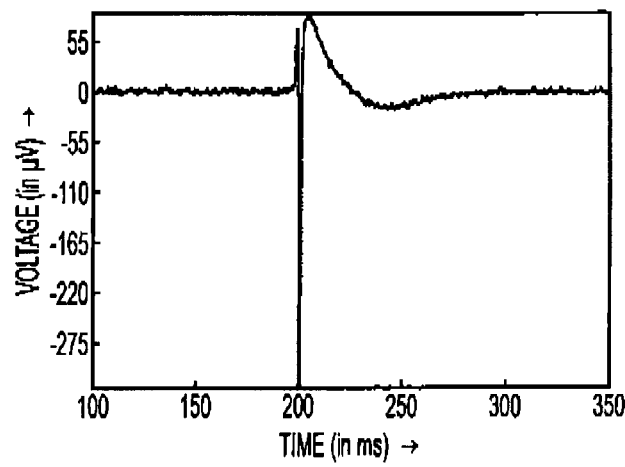
FIG. 11D displays a corresponding action potential as measured by a conventional multi-electrode array.

FIG. 10 shows a time vs. cell concentration plot for the three sets. All three curves increase exponentially until days 4-5, when the cell concentration rate reduces or even drops in one case (with Sylgard). The growth rate for the Sylgard and the porous membrane were comparable and were both larger than the control growth rate.

Experiment 3

On day 0, HeLa Cx43 cells were stained with DiI fluorescent dye and plated on the first surface of a porous membrane as described herein. On day 1, the membrane was turned over, and the second surface of the porous membrane was plated with another set of HeLa cells. These cells were loaded with CellTracker™ Green CMFDA (also known as Green Tracker). Following application of the two cellular layers, the porous membrane preparation was incubated for 6-8 hours. After incubation, the preparation was observed under the microscope in UV light through red and green filters, with red-stained cells with green dye indicating coupling across the two cellular layers through the porous membrane.

The HeLa Cx43 cells were successfully plated on both sides of the porous membrane and showed normal cell growth on visual inspection under the microscope. Each cell layer was viewed after modifying the microscope focus. Using the red filter, the microscope was focused to the red-stained cells' level. The filter was changed to green and cells that appeared focused with the green dye were spotted. The microscope was then focused to the top layer to identify the prospective donor cell across the membrane. Multiple pairs of cells that transferred the green dye across the membrane were spotted. FIGS. 11A-11D show one such case.

Experiment 4

An electrophysiological recording device was positioned within a housing as disclosed herein. The complete and assembled system was washed with PBS and ethanol, and dry-autoclaved at 120° C. The system was then placed in a 60 mm Petri dish to maintain the cells in culture medium. Before plating the cells, the porous membrane was hydrated and treated with fibronectin. Hydration of the porous membrane was achieved by leaving the system in PBS solution for 6-8 hours. Fluid soaked through the air filled pores of the porous membrane, allowing fluid movement across the membrane. The porous membrane was soaked for 1 hour in 2 µg/ml fibronectin solution to promote cell adhesion to the membrane. Neonatal myocytes were isolated and the equivalent to 6-8 hearts was plated on the first surface of the porous membrane. 300 µM Bromodeoxyuridine (BrdU) was added to the cell culture media (DMEM) to restrict fibroblast growth. (DMEM solution: HyQ DMEM/High Glucose; 10%

FBS Fetal Bovine Serum, 1% Pen Strep [10000 ui Penicilin, 10,000 ug/ml Streptomicin, 25 ug/ml Amphoterecin B], 1% L-Glutamine 200 mM and 1% Non-essential-amino acids).

After the cells were plated, the housing was left in the incubator (37° C., 6% $CO_2$, moisture) for 36-48 hours. During this time, the cell culture media was changed every 48 hours.

Before electrophysiological recordings, the culture media was exchanged for OptiMEM (DMEM with Hepes pH buffer) and incubated for 60-90 minutes for acclimatization. After acclimatization, the 60 mm Petri dish containing the housing was positioned in a customized HCMIS micro-incubator. The micro-incubator maintained the preparation at temperatures between 37-38° C. A single-piece electrical connector provided an electrical connection between twenty electrodes of the elecrophysiological recording device and a multi-electrode array amplifier. The signals from the preparation were recorded and stored using MCRack software on a computer. Recordings were taken at a sampling rate of 5 kHz.

After recordings were completed, the system was unplugged from the data acquisition equipment, the cell culture media in the Petri dish was changed back to 300 μM BrdU DMEM solution and left for incubation.

FIGS. 12A-12D show the signals recorded from the 20 recording electrodes on the electrophysiological recording device on day 1 after plating. Signals recorded at electrodes 21, 24, 33, 34, 44 and 51 can be clearly identified as action potentials (refer to FIG. 12). Action potential shape was comparable to signals recorded from cardiomyocyte preparations in a standard MEA. FIGS. 12C-12D show one such selected pair of action potentials from the porous membrane and a standard MEA. FIG. 6.4(B) shows a constant beat rate of 33 beats per minute. The identified action potentials measured a signal to noise ratio (SNR) of 8.6 and peak to peak voltage ($V_{pp}$) of 200 μV.

Experiment 5

An electrophysiological recording device as described herein was fabricated. The electrophysiological recording device was developed on top of a porous membrane made from PCTE. The fabrication steps are as shown in FIGS. 7A-7L.

Initially, a glass slide with a clean surface was selected. AZ P4620 photoresist was spun on the glass slide at 2500 rpm for 50 seconds to form an 8-10 um thick photoresist layer. The resulting wafer was then baked at 90° C. for 5 minutes on a hot plate to give the photoresist a smooth and uniform surface. The porous membrane was cut appropriately and placed on the photoresist layer.

The wafer and porous membrane were baked together, generating bubble-like wrinkles on the membrane. These wrinkles were wiped off gently, and the wafer and porous membrane were cooled. The porous membrane was then coated with parylene using a SCS PDS 2010 parylene coater. The low pressure vapor deposition process (LPCVD) consumed 0.88 grams of parylene dimer to produce a uniform parylene coating (layer 1) of 445 nm thickness on all exposed surfaces including the walls of the pores.

The parylene layer was etched for 30 seconds with an Oxford Plasmalab 80 Plus system using oxygen as the etching gas to improve adhesion of the gold electrodes. A TMV SS-40C-IV, Multi Cathode Sputtering system was used to deposit Titanium oxide (TiO) followed by gold (Au) over the parylene surface. The deposited titanium oxide and gold layer had a total thickness of 93.1 nm. Lithography was used to pattern the metal/conducting layer.

The wafer was spin coated with photoresist (Shipli 1813) at 3000 rpm for 10 seconds and baked at 90° C. for 6 minutes (not shown). The electrode pattern was designed using L-Edit CAD software. The pattern design was printed on a 4" square glass plate in the Electromask MM250 pattern generator. The photoresist layer was then exposed to Ultra Violet (UV) light for 8 seconds through the mask. The mask blocked the UV light, exposing only the non-shaded regions of the mask. The wafer was then washed in developer 352 solution for 50 seconds until the exposed photoresist dissolved. The wafer with the remaining photoresist pattern was washed in deionized water (DI water), dried and exposed to UV light for another 8 seconds. Since gold was shielding the photoresist at the bottom layer, only the patterned photoresist layer was exposed. The wafer was then washed in (Potassium Iodide/Iodine) $KI/I_2$ solution for about 30 seconds to remove the uncovered gold. The wafer was then washed in DI water, dipped in Buffered Oxide Etch (BOE) solution for 10 seconds and again washed in DI water. Once the electrodes were patterned, the solution was washed in developer 352 for 50 seconds to remove the remaining patterned photoresist.

To insulate the lead portions of the electrodes, another layer of parylene (layer 2) was deposited and patterned. Deposition was done in the SCS PDS 2010 parylene coater using 0.92 grams of dimer to obtain a second coat of thickness 650 nm. Patterning of both parylene layers was done by lithography as above, but with a different mask and an additional alignment step with the existing gold pattern on the wafer. Mask-wafer alignment was done using a EVG 420 mask aligner. Once aligned, the photoresist layer was exposed to UV light for 8 seconds, washed in developer 352 to dissolve the exposed photoresist, followed by rinsing in DI water and drying. The wafer was then etched, implementing an anisotropic process—Reactive Ion Etching (RIE)—in the Oxford Plasmalab 80. RIE was carried out for 7 minutes to remove the uncovered parylene layers and pattern the parylene.

The wafer was then soaked in AZ400K solution with gently stirring to peel off the newly formed electrophysiological recording device. After the electrophysiological recording device came off, it was washed in DI water and dried. The electrophysiological recording device was handled using forceps and stored in a 35 mm Petri dish. The electrophysiological recording device was washed with phosphate buffered saline (PBS) and ethanol, followed by an autoclaving process to sterilize it before cell culture.

EQUIVALENTS

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. An electrophysiological recording system for analysis of cultured cells, the electrophysiological recording system comprising:
    an electrophysiological recording device comprising:
        a porous membrane having a top surface and an opposed bottom surface, the porous membrane defining a first cell culture region disposed on a select portion of the top surface and an opposed second cell culture region disposed on a select portion of the bottom surface, the porous membrane further defining a plurality of pores extending between the opposed first and second cell culture regions on the respective opposed top and bottom surfaces; and
        an electrode array comprising a patterned layer that defines a plurality of electrodes, each electrode of the plurality of electrodes having a distal recording end and a proximal contact end, wherein the distal recording end of each electrode of the plurality of electrodes is secured to the porous membrane and extends to the first cell culture region of the porous membrane, wherein the recording ends of the plurality of electrodes are configured for measurement of electrical properties of cells cultured within the first and second cell culture regions on the respective opposed top and bottom surfaces, wherein the contact ends of the plurality of electrodes are configured for electrical communication with data acquisition equipment, and wherein portions of the first and second cell culture regions proximate the recording ends of the plurality of electrodes define a recording portion of the porous membrane; and
    a housing defining a cell culture chamber, wherein at least a portion of the recording portion of the porous membrane is mountable within the cell culture chamber of the housing,
    wherein the porous membrane and the electrode array of the electrophysiological recording device cooperate to form a cell culture structure and are configured to be rolled up together from a substantially planar configuration to form a three-dimensional cell culture structure having a spiral cross-sectional shape, and wherein the housing comprises means for rolling up the porous membrane and the electrode array to form the three-dimensional cell culture structure.

2. The electrophysiological recording system of claim 1, further comprising means for culturing cells on the top surface and the bottom surface of the porous membrane within the opposed first and second cell culture regions.

3. The electrophysiological recording system of claim 2, wherein the cells cultured on the top surface of the porous membrane differ from the cells cultured on the bottom surface of the porous membrane.

4. The electrophysiological recording system of claim 1, further comprising a Petri dish, wherein the cell culture chamber of the housing is configured for receipt therein the Petri dish.

5. The electrophysiological recording system of claim 1, wherein the respective contact ends of adjacent electrodes of the plurality of electrodes are spaced apart from one another at at least one predetermined distance and the respective recording ends of adjacent electrodes of the plurality of electrodes are spaced apart from one another at at least one predetermined distance.

6. The electrophysiological recording system of claim 1, wherein the porous membrane has a thickness ranging from about 5 micrometers to about 15 micrometers.

7. The electrophysiological recording system of claim 1, wherein each pore of the plurality of pores of the porous membrane has a diameter ranging from about 2 micrometers to about 4 micrometers.

8. The electrophysiological recording system of claim 1, wherein the plurality of pores of the porous membrane are present at a density ranging from about 150,000 pores per square centimeter to about 250,000 pores per square centimeter.

9. The electrophysiological recording system of claim 8, wherein the plurality of pores of the porous membrane are randomly scattered within the opposed first and second cell culture regions.

10. The electrophysiological recording system of claim 1, further comprising means for inducing an action potential in cells cultured within at least one of the first cell culture region and the second cell culture region.

11. The electrophysiological recording system of claim 1, wherein the means for inducing an action potential comprises at least one electrode of the plurality of electrodes that is configured to stimulate electrical activity within the recording portion of the porous membrane.

12. The electrophysiological recording system of claim 1, wherein the means for rolling up the porous membrane and the electrode array is configured to form a three-dimensional cell culture having a substantially spiral cross-sectional shape.

13. The electrophysiological recording system of claim 1, wherein the means for rolling up the porous membrane and the electrode array comprises a gear assembly that comprises: a rod configured for attachment to at least a portion of the recording portion of the porous membrane; and at least one gear coupled to the rod and rotatable about a rotation axis, wherein rotation of the at least one gear about the rotation axis results in a corresponding rotation of the rod.

14. The electrophysiological recording system of claim 13, wherein the rod comprises a rod electrode configured for measurement of electrical properties of the formed three-dimensional cell culture and for electrical communication with the data acquisition equipment.

15. The electrophysiological recording system of claim 1, wherein the electrophysiological recording device further comprises:
    a first insulation layer positioned therebetween at least a portion of each electrode of the plurality of electrodes and the top surface of the porous membrane; and
    a second insulation layer positioned thereon at least a portion of each electrode of the plurality of electrodes such that a lead portion of each electrode is positioned therebetween the first insulation layer and the second insulation layer.

16. The electrophysiological recording system of claim 15, wherein the first insulation layer is applied thereon the top surface of the porous membrane and thereon at least a portion of the plurality of pores defined by the porous membrane.

17. The electrophysiological recording system of claim 16, wherein the first insulation layer is applied as a continuous layer across a portion of the top surface of the porous membrane and within and across at least a portion of the plurality of pores defined by the porous membrane.

18. The electrophysiological recording system of claim 15, wherein at least one of the first insulation layer and the second insulation layer comprises parylene.

19. The electrophysiological recording system of claim 1, wherein the housing comprises:
a first base support portion defining an opening;
a second base support portion configured to support the porous membrane such that at least a portion of the opposed first and second cell culture regions of the porous membrane overlie the opening of the first base support portion; and
a first cover portion defining an opening, the first cover portion configured for attachment thereto the first base support portion such that the opening of the first cover portion is substantially aligned with the opening of the first base support portion,
wherein the respective openings of the first base support portion and the first cover portion cooperate to define the cell culture chamber of the housing.

20. The electrophysiological recording system of claim 19, wherein the first cover portion is selectively removable from the electrophysiological recording device.

21. The electrophysiological recording system of claim 19, wherein the first base support portion and the second base support portion are of unitary construction.

22. The electrophysiological recording system of claim 21, wherein the means for rolling up the porous membrane and the electrode array comprises a gear assembly that comprises:
a rod configured for attachment to at least a portion of the recording portion of the porous membrane; and
at least one gear coupled to the rod and rotatable about a rotation axis, wherein rotation of the at least one gear about the rotation axis results in a corresponding rotation of the rod.

23. The electrophysiological recording system of claim 22, wherein the rod comprises a rod electrode configured for measurement of electrical properties of the three-dimensional cell culture and for electrical communication with the data acquisition equipment.

24. The electrophysiological recording system of claim 23, wherein the at least one gear comprises a first gear and a second gear, and wherein the means for rolling up the porous membrane and the electrode array further comprises a first groove and a second groove defined within the first base support portion of the housing, the first groove configured for receipt of the first gear and the second groove configured for receipt of the second gear, wherein the first groove is spaced apart from the second groove along common rotation axis of the respective first and second gears.

25. The electrophysiological recording system of claim 24, wherein the first groove and the second groove are positioned on opposed sides of the opening of the first base support portion.

26. The electrophysiological recording system of claim 19, wherein the housing further comprises a second cover portion, the second cover portion being configured to selectively overlie the second base support portion.

27. The electrophysiological recording system of claim 19, wherein the first base support portion defines a channel in communication with the opening of the first base support portion, and wherein the first cover portion defines a channel in communication with the opening of the first cover portion.

28. An electrophysiological recording system for analysis of cultured cells, the electrophysiological recording system comprising: an electrophysiological recording device comprising:
a porous membrane having a top surface and an opposed bottom surface, the porous membrane defining a first cell culture region disposed on a select portion of the top surface and an opposed second cell culture region disposed on a select portion of the bottom surface, the porous membrane further defining a plurality of pores extending between the opposed first and second cell culture regions on the respective opposed top and bottom surfaces; and
an electrode array comprising a patterned layer that defines a plurality of electrodes, each electrode of the plurality of electrodes having a distal recording end and a proximal contact end, wherein the distal recording end of each electrode of the plurality of electrodes is secured to the porous membrane and extends to the first cell culture region of the porous membrane, wherein the recording ends of the plurality of electrodes are configured for measurement of electrical properties of cells cultured within the first and second cell culture regions on the respective opposed top and bottom surfaces, wherein the contact ends of the plurality of electrodes are configured for electrical communication with data acquisition equipment, and wherein portions of the first and second cell culture regions proximate the recording ends of the plurality of electrodes define a recording portion of the porous membrane; and
a housing defining a cell culture chamber, wherein at least a portion of the recording portion of the porous membrane of the three-dimensional cell culture structure is positioned within the cell culture chamber of the housing,
wherein the porous membrane and the electrode array of the electrophysiological recording device are rolled up together to form a three-dimensional cell culture structure having a spiral cross-sectional shape, and wherein the housing comprises means for rolling up the porous membrane and the electrode array to form the three-dimensional cell culture structure.

29. The electrophysiological recording system of claim 28, wherein the cell culture structure is rolled up into a plurality layers to produce the spiral cross-sectional shape, and wherein adjacent layers of the three-dimensional cell culture structure are spaced apart by a distance ranging from about 1 μm to about 20 μm.

* * * * *